US006743444B2

(12) United States Patent
Jones et al.

(10) Patent No.: US 6,743,444 B2
(45) Date of Patent: Jun. 1, 2004

(54) METHOD OF MAKING MICROENCAPSULATED DNA FOR VACCINATION AND GENE THERAPY

(75) Inventors: David Hugh Jones, Salisbury (GB); Graham Henry Farrar, Salisbury (GB); James Christopher Stephen Clegg, Salisbury (GB)

(73) Assignee: Microbiological Research Authority (GB)

( * ) Notice: Subject to any disclaimer, the term of this patent is extended or adjusted under 35 U.S.C. 154(b) by 0 days.

(21) Appl. No.: 09/898,105

(22) Filed: Jul. 3, 2001

(65) Prior Publication Data

US 2002/0034551 A1 Mar. 21, 2002

Related U.S. Application Data

(62) Division of application No. 09/079,400, filed on May 15, 1998, now Pat. No. 6,270,795, which is a continuation of application No. 08/745,515, filed on Nov. 12, 1996.

(30) Foreign Application Priority Data

| | | |
|---|---|---|
| Nov. 9, 1995 | (GB) | 9523019 |
| Jan. 31, 1996 | (GB) | 9601929 |
| May 15, 1997 | (GB) | 9709900 |

(51) Int. Cl.[7] .......... A61K 9/22
(52) U.S. Cl. .......... 424/468; 424/489; 424/490; 424/497; 514/44; 435/320.1
(58) Field of Search .......... 424/468, 489, 424/490, 497, 93.2; 514/44; 435/320.1, 455

(56) References Cited

U.S. PATENT DOCUMENTS

| | | | |
|---|---|---|---|
| 3,520,970 A | 7/1970 | Lehmann et al. | |
| 3,523,906 A | 8/1970 | Vrancken et al. | |
| 3,737,337 A | 6/1973 | Schnoring et al. | |
| 3,775,537 A | 11/1973 | Lehmann et al. | |
| 3,821,422 A | 6/1974 | Morse et al. | |
| 3,835,221 A | 9/1974 | Fulberth et al. | |
| 3,860,733 A | 1/1975 | Morse et al. | |
| 3,943,063 A | 3/1976 | Morishita et al. | |
| 3,954,959 A | 5/1976 | Pedersen | |
| 3,972,999 A | 8/1976 | Tsuk | |
| 4,016,254 A | 4/1977 | Seager | |
| 4,083,949 A | 4/1978 | Benedikt | |
| 4,182,778 A | 1/1980 | Hall et al. | |
| 4,262,090 A | 4/1981 | Colby, Jr. et al. | |
| 4,293,539 A | 10/1981 | Ludwig et al. | 424/19 |
| 4,321,253 A | 3/1982 | Beatty | |
| 4,384,975 A | 5/1983 | Fong | |
| 4,462,839 A | 7/1984 | McGinley et al. | |
| 4,518,433 A | 5/1985 | McGinley et al. | |
| 4,623,588 A | 11/1986 | Nuwayser et al. | 428/402.24 |
| 4,637,905 A | 1/1987 | Gardner | |
| 4,652,441 A | 3/1987 | Okada et al. | |
| 4,711,782 A | 12/1987 | Okada et al. | |
| 4,741,872 A | 5/1988 | De Luca et al. | 264/4.7 |
| 4,818,542 A | 4/1989 | De Luca et al. | 424/491 |

(List continued on next page.)

FOREIGN PATENT DOCUMENTS

| | | |
|---|---|---|
| CA | 2126685 | 5/1994 |
| EP | 0 027 662 A1 | 4/1981 |
| EP | 0 122 036 | 10/1984 |
| EP | 0127713 | 12/1984 |
| EP | 0 145 240 | 6/1985 |
| EP | 0 161 640 | 11/1985 |
| EP | 0 179 023 A2 | 4/1986 |
| EP | 0 248 531 | 9/1987 |
| EP | 0 250 038 A2 | 12/1987 |
| EP | 0 257 915 | 3/1988 |
| EP | 0 258 749 A2 | 3/1988 |
| EP | 0 263 490 | 4/1988 |
| EP | 0266119 | 5/1988 |
| EP | 0302582 | 2/1989 |
| EP | 0330180 | 8/1989 |

(List continued on next page.)

OTHER PUBLICATIONS

Morris, W. et al., "Potential of polymer microencapsulation technology for vaccine innovation," *Vaccine,* vol. 12, No. 1, pp. 5–11 (1994).

Epstein, D.A. et al., "Alternative Delivery Systems For Peptides And Proteins As Drugs," *CRC Critical Review in Therapuetic Drug Carrier Systems,* vol. 5, Issue 2, pp. 99–139 (1988).

Rajasubramanian, Ganesh et al., "Fabrication of Resorbable Microporous Intravascular Stents for Gene Therapy Applications", *ASAIO Journal,* vol. 40, No. 3, pp. 584–589 (Jul. 1994).

Morris, William et al., "Potential of Polymer Microencapsulation Technology for Vaccine Innovation", *Vaccine,* vol. 12, No. 1, pp. 5–11 (Jan. 1994).

Sah, H. K. et al., "Biodegradable Microcapsules Prepared by a W/O/W Technique: Effects of Shear Force to Make a Primary W/O Emulsion on their Morphology and Protein Release", *Journal of Microencapsulation,* vol. 12, No. 1, pp. 59–69 (Jan. 1995).

(List continued on next page.)

*Primary Examiner*—Dave T. Nguyen
(74) *Attorney, Agent, or Firm*—Fish & Richardson P.C.

(57) ABSTRACT

A method of making a microparticle that contains DNA coding for a polypeptide is described in which a solvent extraction method is used and solvent extraction takes place at elevated temperature. Oral administration of the microparticle leads to its expression. DNA coding for an immunogen is for stimulating antibody formation in a recipient and DNA coding for a non-immunogenic polypeptide is for gene therapy applications. DNA is incorporated into the microparticle without destruction of its function.

26 Claims, 10 Drawing Sheets

U.S. PATENT DOCUMENTS

| | | | | |
|---|---|---|---|---|
| 4,853,226 | A | | 8/1989 | Machida et al. |
| 4,897,268 | A | | 1/1990 | Tice et al. |
| 4,917,893 | A | | 4/1990 | Okada et al. |
| 4,933,105 | A | | 6/1990 | Fong |
| 5,061,492 | A | | 10/1991 | Okada et al. |
| 5,075,109 | A | | 12/1991 | Tice et al. |
| 5,084,553 | A | | 1/1992 | Hess et al. .................. 526/361 |
| 5,100,669 | A | | 3/1992 | Hyon et al. |
| 5,126,147 | A | | 6/1992 | Silvestri et al. |
| 5,160,745 | A | | 11/1992 | DeLuca et al. ............. 424/487 |
| 5,180,765 | A | | 1/1993 | Sinclair |
| 5,279,708 | A | | 1/1994 | Wood et al. |
| 5,354,556 | A | | 10/1994 | Sparks et al. |
| 5,366,733 | A | | 11/1994 | Brizzolara et al. |
| 5,407,609 | A | | 4/1995 | Tice et al. |
| 5,413,797 | A | | 5/1995 | Khan et al. |
| 5,417,986 | A | | 5/1995 | Reid et al. |
| 5,460,831 | A | | 10/1995 | Kossovsky et al. |
| 5,531,925 | A | | 7/1996 | Landh et al. |
| 5,540,937 | A | | 7/1996 | Billot et al. |
| 5,580,859 | A | | 12/1996 | Felgner et al. |
| 5,589,466 | A | | 12/1996 | Felgner et al. |
| 5,622,649 | A | | 4/1997 | Hunter et al. |
| 5,622,657 | A | | 4/1997 | Takada et al. |
| 5,639,473 | A | | 6/1997 | Grinstaff et al. |
| 5,643,605 | A | | 7/1997 | Cleland et al. |
| 5,648,095 | A | | 7/1997 | Illum et al. |
| 5,648,096 | A | | 7/1997 | Gander et al. |
| 5,650,173 | A | | 7/1997 | Ramstack et al. |
| 5,651,990 | A | | 7/1997 | Takada et al. |
| 5,652,283 | A | | 7/1997 | Boeckh et al. |
| 5,654,008 | A | | 8/1997 | Herbert et al. |
| 5,656,297 | A | | 8/1997 | Bernstein et al. |
| 5,656,469 | A | | 8/1997 | Tresco et al. |
| 5,662,938 | A | | 9/1997 | Vert et al. |
| 5,665,383 | A | | 9/1997 | Grinstaff et al. |
| 5,690,954 | A | | 11/1997 | Illum |
| 5,700,486 | A | | 12/1997 | Canal et al. |
| 5,723,269 | A | | 3/1998 | Akagi et al. |
| 5,783,567 | A | | 7/1998 | Hedley et al. |
| 5,792,366 | A | | 8/1998 | Coville |
| 5,811,128 | A | | 9/1998 | Tice et al. |
| 5,814,344 | A | | 9/1998 | Tice et al. |
| 5,820,883 | A | | 10/1998 | Tice et al. .................. 424/501 |
| 5,853,763 | A | | 12/1998 | Tice et al. |
| 5,869,103 | A | | 2/1999 | Yeh et al. |
| 5,879,713 | A | | 3/1999 | Roth et al. |
| 5,885,590 | A | | 3/1999 | Hunter et al. |
| 5,891,676 | A | * | 4/1999 | Estes ......................... 435/69.1 |
| 5,919,408 | A | | 7/1999 | Muller et al. |
| 5,945,126 | A | | 8/1999 | Thanoo et al. |
| 6,020,004 | A | | 2/2000 | Shah |
| 6,025,337 | A | | 2/2000 | Truong et al. |
| 6,048,551 | A | | 4/2000 | Hilfinger et al. |
| 6,096,331 | A | | 8/2000 | Desai et al. |
| 6,113,947 | A | | 9/2000 | Cleland et al. |
| 6,159,502 | A | | 12/2000 | Russell-Jones et al. |
| 6,270,795 | B1 | | 8/2001 | Jones et al. |
| 6,309,569 | B1 | | 10/2001 | Farrar et al. |
| 6,475,779 | B2 | * | 11/2002 | Mathowitz ............... 435/320.1 |
| 2002/0192651 | A1 | | 12/2002 | Wheeler et al. |

FOREIGN PATENT DOCUMENTS

| | | | |
|---|---|---|---|
| EP | 0333523 | | 9/1989 |
| EP | 0 334 062 | A2 | 9/1989 |
| EP | 0 374 531 | A2 | 6/1990 |
| EP | 0 451 390 | | 10/1991 |
| EP | 0451391 | | 10/1991 |
| EP | 0 467 389 | A2 | 1/1992 |
| EP | 0471036 | | 2/1992 |
| EP | 0 475 178 | A1 | 3/1992 |
| EP | 0531497 | | 3/1993 |
| EP | 0 635 261 | A1 | 1/1995 |
| EP | 0706792 | | 4/1996 |
| EP | 0737750 | | 10/1996 |
| EP | 0 761 211 | | 3/1997 |
| EP | 0 779 072 | | 6/1997 |
| FR | 2 660 556 | | 10/1991 |
| GB | 2147501 | | 5/1985 |
| GB | 2185979 | A | 8/1987 |
| GB | 2234896 | | 2/1991 |
| GB | 2265311 | A | 9/1993 |
| GB | 2310801 | A | 9/1997 |
| WO | WO 88/08300 | | 11/1988 |
| WO | WO 90/11092 | | 10/1990 |
| WO | 91/11092 | | 10/1990 |
| WO | WO 90/13361 | | 11/1990 |
| WO | WO 91/19487 | | 12/1991 |
| WO | WO 92/06666 | | 4/1992 |
| WO | 93/19183 | | 9/1993 |
| WO | WO 94/04121 | | 3/1994 |
| WO | WO 94/04171 | | 3/1994 |
| WO | 94/04260 | | 3/1994 |
| WO | WO 94/09898 | | 5/1994 |
| WO | WO 94/18954 | | 9/1994 |
| WO | 94/23699 | | 10/1994 |
| WO | WO 94/23738 | | 10/1994 |
| WO | 94/23738 | | 10/1994 |
| WO | WO 94/28873 | | 12/1994 |
| WO | WO 95/03356 | | 2/1995 |
| WO | WO 95/03357 | | 2/1995 |
| WO | WO 95/05853 | | 3/1995 |
| WO | WO 95/07072 | | 3/1995 |
| WO | WO 95/11009 | | 4/1995 |
| WO | WO 95/17167 | | 6/1995 |
| WO | 95/20660 | | 8/1995 |
| WO | 95/21250 | | 8/1995 |
| WO | WO 95/21931 | | 8/1995 |
| WO | 95/24929 | | 9/1995 |
| WO | 95/31184 | | 11/1995 |
| WO | 95/31187 | | 11/1995 |
| WO | 95/35097 | | 11/1995 |
| WO | 95/35097 | | 12/1995 |
| WO | 96/00295 | | 1/1996 |
| WO | WO 96/11671 | | 4/1996 |
| WO | WO 96/29998 | | 10/1996 |
| WO | WO 96/36317 | | 11/1996 |
| WO | WO 97/03702 | | 2/1997 |
| WO | WO 97/17063 | | 5/1997 |
| WO | WO 97/35563 | | 10/1997 |
| WO | 97/36578 | | 10/1997 |
| WO | WO 97/42940 | | 11/1997 |
| WO | WO 88/01213 | | 2/1998 |
| WO | WO 98/31346 | | 7/1998 |
| WO | WO 98/31398 | | 7/1998 |
| WO | WO 98/51279 | | 11/1998 |
| WO | WO 99/58112 | | 11/1999 |
| WO | WO 00/03660 | | 1/2000 |

OTHER PUBLICATIONS

Nellore, Ranjani et al., "Application of Biodegradable Microspheres to Hapatitis B Surface Antigen Vaccination System", *Pharmaceutical Research,* vol. 8, No. 10, p. S151, Abstract No. PDD 7098 (1991).

P. Marquet et al., "Toxicity of tungsten", *The Lancet,* vol. 349, pp. 58–59 (Jan. 4, 1997).

D.L. Miller et al., "Comet Assay Reveals DNA Strand Breaks Induced by Ultrasonic Cavitation In Vitro", *Ultrasound in Med. & Biol.,* vol. 21, No. 6, pp. 841–848 (1995).

Dialog File 351, Accession No. 86–108252/198617, Derwent WPI English language abstract for Document AM1 (EP 0 179 023 A2), 86.

Dialog File 351, Accession No. 92–166845/199220, Derwent WPI English language abstract for Document AL3 (WO 92/06666), 92.

Dialog File 351, Accession No. 94–167187/199420, Derwent WPI English language abstract for Document AN3 (WO 94/09898), 1994.

Amagi, M. et al., "Antibodies Against a Novel *Epithelial cadherin* in *Ppmphigus vulgaris,* a Disease of Cell Adhesion," *Cell* 67:869–877 (1991).

Chen, S.C. et al., "Protective Immunity by Oral Immunization with a Rotavirus DNA Vaccine Encapsulated in Microparticles," *J. Virol.* 72:5757–5761 (Jul. 1998).

Eldridge, J.H. et al., "Biodegradable and Biocompatible Poly)di–lactic–co–glycolide) Microspheres as an Adjuvant for Staphylococcal Enterotoxin B Toxiod Which Enhances the Level of $\alpha\chi$in–neutralizing Antibodies," *Infect. Imm.* 59:2978–2986 (1991).

Eldridge, J.H. et al., "Controlled Vaccine Release in the Gut–Associated Lymphoid Tissues. 1. Orally Administered Biodegradable Microspheres Target the Peyer's Patches," *J. Controlled Release* JI:205–214 (1990).

Florence, A.T. "The Oral Absorption of Micro– and Nanoparticulates: Neither Exceptional Nor Unusual," *Pharm. Res.* 14:259–266 (Mar. 1997).

Gref, R. et al., "Biodegradable Long–Circulating Polymeric Nanopheres," *Science* 263:1600–1603 (1994).

Heard, "HLA and autoimmune disease," in *HLA and Disease,* Academic Press, San Diego, CA, chapter 7 (1994).

Hedly, M. L. "Genetic Modulation and Antigen Presentation," in *MHC Molecule: Expression, Assembly, and Function,* chapter 17 (1996).

Jacobs S.C. et al., "Protection elcited by a replication–defective adenovirus vector expressing the tick–borne encephalitis virus non–structural glycoprotein NS1," *J. Gen. Virol.* 75:2399–2402 (1994).

Jacobs, S.C. et al., "High–Level Expression of the Tick–Borne Encephalitis Virus NS1 Protein by Using an Adenovirus–Based Vector: Protection Elicited in a Murine Model," *J. Virol.* 66:2086–2095 (1992).

Jepson, M. et al., "Comparison of Poly(DL–Lactide–Glycolide) and Polystyrene Microsphere Targeting to Intestinal M Cells," *J. Drug Targeting* 1:245–249 (1993).

Jeyanthi, R. et al., "Development of a Biodegradable Micropshere Formaulation for the Sustained Release of a Bioactive Peptide," *Pharm, Res.* 8:151(S), pdd 7079 (1991).

Jones, D.H. et al., "Orally Administered Microencapsulated *Bordetella pertussis* Finbriae Protect Mice from *B. pertussis* Respiratory Infection," *Infect. Immun.* 64:489–494 (Feb. 1996).

Jones et al., "Poly(DL–lactide–co–glycolide)– encapsulated plasmid DNA elicite systemic and mucosal antibody responses to encoded protein after oral andministration," *Vaccine* 15:814–817 (Jun. 1997).

Jones, et al., "Oral delivery of Poly(lactide–co–glycolide) encapsulated vaccines," *Behring Inst. Mitt.* 98:220–228 (Feb. 1997).

Jones, D.H. et al., "Immune Responses Following Oral and Parental Administration of Plasmid DNA Encapsulated in Poly(lactide–coglycolide) Microparticles," *Int. Meeting on Nucleic Acid Vaccines,* Bethesda, MD, Abstract and attached Figures 2 and 3 and Figure entitled Stool IgA Response to PLG–Encapsulated DNA (Feb. 5–7, 1996).

Jones, D.N. et al., "Oral Delivery of Micro–Encapsulated DNA Vaccines," *Dev. Biol. Stand.* 92:149–155 (1998).

Jones, D.N. et al., "Protection of mice from *Bordetella pertussis* respiratory infection using microencapsulated pertussis fimbrise," *Vaccine* 13:675–681 (May 1995).

Jones, D.N. et al., "PLG microencapsulation of vaccine antigens," *J. Biotech.* 44:29–36 (1994).

Kreuter, J. "Nanoparticles and microparticles for drug and vaccine delivery," *J. Anat.* 189:503–505 (Dec. 1996).

Lewis, K. et al., "Biodegradable poly(L–lactic acid) matrices for the sustained deliveryu of antisense oligonucleotides," *J. Controlled Release* 37:173–183 (Nov. 1995).

Murphy, D. et al., "A novel MNC class II epitope expressed in thymic modulla but not cortex," *Nature* 338:765–768 (1989).

Neutra, M. et al., "Epithelial M Cells: Gateways for Mucosal Infection and Imunization," *Cell* 86:345–348 (Aug. 1996).

D'Hagan, D.T. "The intestinal uptake of particles and the implications for drug and antigen delivery," *J. Anat.* 189:477–482 (Dec. 1996).

Puyal, C. et al., "A new cationic liposome encapsulating genetic material. A potential delivery system for polynucleotides," *Eur J Biochem.* 228:697–703 (Mar. 1995).

Shimoda, S. et al., "HLA–DR84 0101–restricted Immunodominant T Cell Autoepitope of Pyruvate Dehydrogenase Complex in Primary Biliary Cirrhosis: Evidence of Molecular Nimicry in Human Autoimmune Diseases," *J. Exp. Med.* 181:1835–1845 (May 1995).

Seteinman, L. "Escape from Horror Autotoxicus': Pathogenesis and Treatment of Autoimmune Disease," *Cell* 80:7–10 (Jan. 1995).

Tomlinson, E. and Rolland, A.P. et al., "Controllable gene therapy Pharmaceutics of non–viral gene delivery systems," *J. Controlled Release* 39:357–372 (Mar. 1996).

Visscher, G.E. "Biodegradation of and tissue reaction to 50:50 Poly(DL–lactide–co–glycolide) microcapsules," *J. Biomed. Mater. Res.* 19:349–363 (1985).

Dialog File 351, Accession No. 81–329240/198119, Derwent WPI English language abstract for Document AL1 (EP 0 027 662 A1), 86.

Alexakis, T. et al., "Microencapsulation of DNA WithAlginate Microspheres and Crosslinked Chitosan Membranes for In Vivo Application," Appl. Biochem. Biotech. 50:93–106 (1995).

Crystal et al., "Transfer of Genes to Humans: Early Lessons and Obstacles to Success", *Science* 270:404–410 (1995).

English language abstract of Japanese Patent No. 06–009377, 1994.

Etlinger, "Carrier sequence selection–one key to successful vaccines", *Imm. Today* 13:52–55 (1992).

Gunzburg et al., "Virus vector design in gene therapy", *Mol. Med. Today* 1:410–417 (1995).

Ledley, "Nonviral Gene Therapy: The Promise of Genes as Pharmacuetical Products", *Hum. Gen. Ther.* 6:1128–1114 (1995).

Truong, V.L. et al., "Gene Transfer by Gelatin–DNA Coacervate," Proceed. Intern, Symp. Control Rel. Bioact. Mater. 22:466–467 (1995).

Truong, V.L. et al., "Immuno–microsphere as Gene Delivery Vehicle:Targeting of LAMP–I to Lysosomal Membrane," Proceed. Intern. Symp. Control. Rel. Bioact. Mater. 21:142–143 (1994).

Whelan, "DNA vaccines for emerging infectious diseases", *Emerging Infect. Dis.* 2:168–175 (1996).

Yan et al., Journal of controlled Release 32, 231–241 (1994).

Allen et al. "Biological Properties of Equine Herpesvirus Type 1 DNA: Transfectivity and Transferning Capacity" *Infection and Immunity* 22: 34–40 (1978).

Alonso et al. "Determinants of release rate of tetanus vaccine from polyester microspheres" Pharmaceutical Research (New York) 10(7):945–953 (1993).

Alpar et al., "Potential of Particulate Carriers for the Mucosal Delivery of DNA Vaccines," Biochemical Society Transactions, 25:337S, (1997).

Anderson, "Human gene therapy", Nature 392:25–30 (1998).

Bodmeier et al., "The Preparation and Evaluation of Drug–Containing Poly(dl–lactide) Microspheres Formed by the Solvent Evaporation Method," Pharmaceutical Research, 4:465, 466, 571, (1987).

Brayden et al. "Microparticle vaccine . . . immunization", Microbes and Infection 3:867–876 (2001).

Chang, "Biodegradable Semipermeable Microcapsules Containing Enzymes, Hormones, Vaccines, and Other Biologicals" Journal of Bioengineering, 1:25–32 (1976).

Chasin et al. (Editors), "Biodegradable Polymers as Drug Delivery Systems", University of Washington Libraries, pp. 1–41, 1990.

Cowsar et al., "Poly(lactide–co–glycolide) Microcapsules for Controlled Release of Steroids", Methods in Enzymology, 112,pp. 101–117 (1985).

Elsner et al., "Ultrasonic Degradation of DNA" *DNA* 8:697–701 (1989).

Ghaderi et al., "Effect of preparative parameters on the characteristics of poly(D, L–lactide–co–glycolide) microspheres made by the double emulsion method" Int. J. Pharm. 141(1,2):205–216, (1996).

Jones et al. "Poly(lactide–co–glycolide) microencapsulation of vaccine antigens", *J. Biotech* 44: m29–36 (1994).

Li, "Nonviral gene therapy: promises and challenges", Gene Therapy 7:31–34 (2000).

McCluskie et al., "Route and Method of Delivery of DNA Vaccine Influence Immune Responses in Mice and Non–Human Primates", Molecular Medicine 5:287–300.

Nakano et al., "Sustained Urinary Excretion of Sulfamethizole Following Oral Administration of Enteric Coated Microcapsules in Humans," Int'l. Journal of Pharmaceutics, 4:291–298, (1980).

Ngo et al., "Computational Complexity, Protein Structure Prediction, and the Levinthal Paradox", Birkhauser Boston 14:492–495 (1994).

Partidos et al., "Biodegradable Microparticles as a Delivery System for Measles Virus Cytotoxic T Cell Epitopes," Molecular Immunology 33(6):485–491 (1996).

Spooner et al. "DNA vaccination for cancer treatment", Gene Therapy 2, 173–180 (1995).

Tinsley–Brown et al., *J. Con. Rel.* 66:229–241 (2000).

Uchida et al. "Oral Delivery of Poly(lactide–co–glycolide) Microspheres Containing Oviabumin as a Vaccine Formulation: Particle Size Study" Biol. Pharm. Bull. 17(9):1272–1276 (1994).

Urban et al., "The Discovery and Use of HLA–Associated Epitopes as Drugs," Critical Reviews in Immunology, 17:387–397 (1997).

Verrth et al., "Gene therapy–promises, problems and prospects", Nature 389:239–242 (1997).

Wang et al., "Encapsulation of Plasmid DNA. . . Gene Delivery", J8: Synthetic Non–Viral Gene Delivery Systems, Keystone, CO, Abst. No. 120, Jan. 19–25, 1998 p. 132.

Wheeler et al. "Immunogenecity in Guinea Pigs and Tolerance in Grass Pollen–Sensitive Volunteers of Enteric–Coated Grass Pollen Allergens", Int. Archs. Allergy appl. Immun. 83:354–358 (1987).

Wheeler, "Stabilized plasmid–lipid particles: construction and characterization", Gene Therapy 6:721–(1999).

Wolff et al. "Direct Gene Transfer into Mouse Muscle in Vivo" Science 247:1465–1468 (1990).

Woodle, "New Amphipatic Polymer. . . Liposomes", Bioconjugate Chemistry 5:494–496 (1994).

* cited by examiner

METHOD OF MAKING MICROENCAPSULATED DNA FOR VACCINATION AND GENE THERAPY

CROSS-REFERENCE TO RELATED APPLICATIONS

This application is a divisional of U.S. Ser. No. 09/079,400, filed May 15, 1998 now U.S. Pat. No. 6,270,795, which is a continuation of U.S. Ser. No. 08/745,515, filed Nov. 12, 1996; and claims priority under 35 U.S.C. §119 from United Kingdom Application 9523019.9, filed Nov. 9, 1995, United Kingdom Application 9601929.4, filed Jan. 31, 1996, PCT Application GB96/02770, filed Nov. 11, 1996, and United Kingdom Application 9709900.6, filed May 15, 1997.

FIELD OF THE INVENTION

The present invention relates to microencapsulated DNA, to vaccines comprising microencapsulated DNA, to methods of vaccination and to methods of gene therapy comprising administration of DNA in microparticles, to methods of preparing microparticles containing DNA and to dried compositions comprising DNA-containing particles.

BACKGROUND OF THE INVENTION

The bio-degradable polymer poly (DL-lactide-co-glycolide) (PLG) has been used for many years by the pharmaceutical industry to deliver drugs and biologicals in microparticulate form in vivo. The United States FDA has recently approved a PLG microsphere 30-day delivery system for leuprolide acetate (Lupran Depot (registered trade mark)) to be used in the treatment of prostate cancer. A useful review of the potential of polymer microencapsulation technology for vaccine use is found in Vaccine, 1994, volume 12, number 1, pages 5–11, by William Morris et al.

As an alternative to encapsulation, it is also known to deliver antigens in phospholipid vesicles called liposomes, as described for example by Eppstein, D. A et al in Crit. Rev. Ther. Drug Carrier Syst. 1988, 5(2), pages 99–139. It is reported that a number of antigens have been delivered intraperitoneally using liposomes, including cholera toxin, malaria sporozoite protein and tetanus toxoid, and that influenza antigen has been delivered intra-nasally.

It is also known that, in certain circumstances, injection of naked DNA into tissue can lead to expression of a gene product coded by that DNA. For example, in 1984, work at the United States NIH reported that intrahepatic injection of naked, cloned plasmid DNA for squirrel hepatitis produced both viral infection and the formation of anti-viral antibodies in the squirrels.

WO-A-95/05853 describes methods, compositions and devices for administration of naked polynucleotides which encode biologically active peptides. This published application describes, inter alia, the injection of naked DNA coding for an immunogenic antigen with the aim of raising antibodies in the recipient of the naked DNA.

Liposomal delivery of DNA is also known, and is described, for example, in EP-A-0475178.

An alternative method for obtaining in vivo expression of a desired gene product is described in EP-A-0161640, in which mouse cells expressing bovine growth hormone are encapsulated and implanted into a cow to increase milk production therein.

EP-A-0248531 describes encapsulating linear poly (I:C) in microcapsules and using these to induce production of interferon.

WO-A-94/23738 purports to describe a microparticle containing DNA in combination with a conjugate that facilitates and targets cellular uptake of the DNA. In working examples, bombardment of cells by microparticles containing Tungsten is described. These examples appear little different to conventional bombardment of cells with DNA-coated metal particles. Furthermore, sonication is proposed in microparticle manufacture, a step that is known to risk DNA damage, and the presented data is inadequate and inappropriate to determine the integrity of the encapsulated DNA.

In the present invention, it is desired to deliver, in vivo, DNA that encodes proteins with immunogenic, enzymatic or other useful biological activity, usually under the control of an active eukaryotic promoter. Objects of the invention include improvement on vaccination therapies known in the art and improvement upon prior art gene therapy methods. Improvement of or alternatives to existing compositions and methods are desirable as these existing methods are known to contain a number of drawbacks.

WO-A-95/05853 describes administration of naked polynucleotides which code for desired gene products. However, the compositions and methods in this publication are suitable only for injection, requiring sterile procedures, and being in itself an unpleasant and awkward route of administration.

WO-A-94/23738 purports to provide a process in which encapsulated DNA is released from particles in the body of the recipient and then taken up by cells, although no accomplished in vivo examples are presented.

Morris W et al ('Potential of polymer microencapsulation technology for vaccine innovation', Vaccine, Vol. 12, No. 1; pp5–11) is an article reviewing the PLG encapsulation field. It does not describe delivering DNA based vaccines. Instead, it describes delivering antigen based vaccines. Further, it only fleetingly describes preparation of microparticles that contain an internal component within a polymer shell. Instead, it primarily describes microparticles of the matrix type, that is to say within which an antigen is dispersed. Morris et al define such particles as "microspheres"—see page 5, column 2, lines 20–22—and the article deals extensively with such microspheres. Morris et al refer to a polymer shell that encapsulates an internal component as a "microcapsule".

The small section in the Morris paper on how to obtain microcapsules, from page 8, middle of column 2 to the top of column 1 on page 9 describes microcapsules of >50 $\mu$l in volume (about 1.2 mm in diameter).

Sah H K et al ('Biodegradeable microcapsules prepared by a w/o/w technique: effects of shear force to make a primary w/o emulsion on their morphology and protein release' J. Microencapsulation, Vol. 12, No. 1, 1995, pp59–69) describes a water-in-oil-in-water method for the encapsulation of biologically active agents. The thrust of the article is on determining the influence of shear forces on the characteristics of the microcapsules obtained. We refer to the first two lines of the abstract. The size distribution of these particles was measured and found to be in the range 10–75 $\mu$m. Further, Sah et al were not able to change the size of the microcapsules that they prepared. We refer again to the second paragraph in "Results and discussion" towards the end, where it is stated:

> "However, in our experiments, the change of sheer rate from 11 to 23 krpm to produce the primary W/O emulsion did not result in a reduction in microcapsule size. No correlation between shear forces to make an initial W/O emulsion and the resulting microcapsule size was observed".

Many published patents and applications are in the name of the Southern Research Institute (SRI). In particular, U.S. Pat. No. 5,407,609 purports to describe in example 7, an emulsion based method for the manufacture of hollow particles. However, the methods detailed in U.S. Pat. No. 5,407,609 succeed in making relatively large particles, or at least particles over a wide range of sizes, where a significant portion of particles are larger than the biological activity cut off point of 10 microns. A large spread of particle sizes, such as that seen in U.S. Pat. No. 5,407,609 inevitably leads to much of the encapsulated agent being incorporated in particles of a size that are not appropriate for phagocytosis.

The invention seeks to provide novel compositions and methods of administration thereof that improve upon existing vaccination and gene therapy techniques and are effective in vivo, or at least overcome some of the problems or disadvantages identified in known compositions and methods.

It is known that DNA is readily damaged so that it is no longer capable of inducing expression of a gene product. Surprisingly, the inventors have succeeded in devising a technique for encapsulation of DNA within polymer particles, such that the DNA retains sufficient integrity to induce expression of a gene product coded thereby. The inventors have also succeeded in devising a DNA-containing microparticle suitable for mammalian vaccination or for gene therapy.

Accordingly, a first aspect of the invention provides a composition for expression of a DNA coding sequence in a recipient, the composition comprising a polymer microparticle and DNA, wherein the DNA is in aqueous solution, is inside the microparticle and comprises said coding sequence, and wherein the microparticle is 10 $\mu$m or less in diameter and induces expression of said coding sequence following oral administration to a recipient.

Preferably, the polymer is soluble in organic solvent and thereby suitable for formation of microparticles by solvent extraction.

A second aspect of the invention provides a method of encapsulating DNA in a polymer microparticle, comprising providing a (water-in-oil)-in-water emulsion, adding this emulsion to excess of a further aqueous phase to extract the oil phase and thereby form microparticles, wherein the further aqueous phase is added at elevated temperature.

The method enables useful biological activity, ie transducing activity, of the DNA to be retained in the microparticle which is suitable for vaccination and/or gene therapy depending upon its coding sequence. Thus, according to the method of the invention, an aqueous solution of DNA is prepared and added to an oil phase with agitation to form a water-in-oil emulsion. The water droplets in this emulsion contribute the aqueous DNA in the final microparticle. This emulsion is added to a second aqueous phase, forming the double (water-in-oil)-in-water emulsion, and extraction of solvent at elevated temperature leads to improved incorporation of DNA into the microparticle.

In an embodiment of the second aspect, a method for encapsulating DNA within a polymer particle, said DNA being capable of inducing expression of a coding sequence within said DNA, comprises preparing a (water-in-oil)-in-water emulsion to form microparticles and separating subsequently produced DNA-containing microparticles by centrifugation. Resultant microparticles preferably have sizes in the range 0.01 $\mu$m to 30 $\mu$m, more preferably 1 $\mu$m to 10 $\mu$m.

The method of the invention is carried out under conditions that ensure at least a minimum portion of the DNA is not damaged during manufacture of the particles and thereby retains its ability to induce expression of its gene coding sequence.

A typical method of the invention comprises:

(a) preparing an aqueous solution of DNA, said DNA comprising a sequence coding for a polypeptide in operative combination with at least a promoter sequence and optionally other sequences regulating or otherwise directing transcription of the DNA, said DNA being adapted to express the polypeptide in a mammalian recipient;

(b) preparing a solution of polymer in an organic solvent;

(c) forming an emulsion of the aqueous DNA solution in the organic polymer solution;

(d) preparing an aqueous surfactant solution;

(e) forming a double emulsion of (I) the emulsion from (c) in (II) the aqueous surfactant solution;

(f) at elevated temperature, dispersing or otherwise removing the organic solvent so as to form microparticles of polymer having sizes up to 10 $\mu$m in diameter and which contain said DNA; and (g) recovering the microparticles.

Recovery of microparticles from the solution is optionally by centrifuging the solution to form a pellet of microparticles, separating the pellet from the supernatant solution and resuspending the pellet in a desired solution, typically water. This step is conveniently repeated several times to prepare a purified preparation.

It is essential that step (f) is carried out so as to disperse or otherwise remove the organic solvent and form microparticles of the desired size without melting of the polymer into a congealed mass. According to the invention, this step is carried out at elevated temperature, that is to say (i) a temperature higher than that for steps (a)–(e), or (ii) a temperature above ambient temperature. The organic solvent used for the oil phase is generally more volatile than water, and it has surprisingly been found that carrying out the dispersal step at elevated temperature promotes uptake of DNA into the microparticle. Suitable above-ambient elevated temperatures are at least 25° C., and preferably at least 30° C. Beyond about 60° C. there is the risk of the organic solvent boiling off, which must of course be avoided. However, with most solvents particularly good results are obtainable at 35° C. and above.

In embodiments of the invention, forming of the double emulsion takes place below ambient temperature, and in these embodiments it is preferred that step (f) be carried out at a temperature at least 5° C. higher, and more preferably at least 10° C. higher.

The elevated temperature suitable to disperse the organic solvent may vary according to the choice of organic solvent. Solvent is removed under conditions that set the polymer into microparticles that contain DNA and avoiding melting of the polymer. In specific embodiments of the invention the organic solvent is dichloromethane and this is efficiently dispersed at a temperature of about 35° C.

It is essential that DNA is incorporated into the microparticles, and DNA incorporation is optionally increased by preparing an aqueous solution of DNA plus an alcohol, adding microparticle polymer and forming microparticles therefrom. The alcohol content of the solution suitably varies between 1% and 60% and preferably between 5% and 40%. The role of the alcohol is to alter the chemistry of the transition from the aqueous to the oil phases, and the advantageous result of using alcohol in this way is to provide for improvements in DNA uptake into the microparticle. In specific embodiments of the invention the alcohol content is around 15–35%, more particularly 20–30% for microparticles made from PLG, producing DNA incorporation of 25% and above, up to 50–60%. Ethanol is particularly suitable; methanol and propanol and other alcohols that do not denature DNA are also suitable, and the alcohol is preferably a straight chain or branched $C_2$–$C_{10}$ alcohol. However, a further feature of using elevated temperature to obtain microparticles from the double emulsion of step (e) is that when an elevated temperature is used for this purpose then it is further an option for the aqueous solution of DNA to contain a lesser amount of alcohol, such as 5% or less, and even to contain no alcohol.

A thus further aspect of the invention resides in a method of encapsulating an aqueous solution of DNA in a polymer microparticle, comprising providing a (water-in-oil)-in-water emulsion containing the DNA solution; and adding this emulsion to excess of a further aqueous phase to extract the oil phase and thereby form microparticles, wherein the aqueous solution of DNA comprises alcohol.

It is also preferred that the emulsification step or steps of the method be carried out under conditions of reduced shear stress, and this is optionally achieved by use of an emulsifying energy, such as speed in the case of an emulsifying mixer, that is sufficient to obtain an emulsion and to form microparticles in the desired size range but not so high that all DNA is damaged by excessive shear. In an embodiment of the invention described below the emulsifying mixer speed is modified so that at least 25% DNA activity (assayed by transformation of competent bacteria or transfection of cultured cells) is retained in the resultant microparticles that contain DNA. Suitable mixer speeds are below 8000 rpm, preferably below 6000 rpm, and in specific embodiments described below the speeds are about 3000 rpm or about 2000 rpm.

A range of surfactants are suitable for use in the method of the invention, and the present invention is not limited to the particular surfactant used in the examples, polyvinylalcohol. Other acceptable surfactants are known in the art. The surfactant has the role of stabilising the double emulsion of aqueous DNA solution in polymer plus organic solvent in surfactant. Choice of aqueous surfactant is a matter for the skilled person and this choice may be made with regard to the choice of polymer and polymer solvent. Likewise, choice of polymer solvent is not limited to that used in the examples, dichloromethane, but encompasses any suitable organic solvent for formation of the double emulsion and subsequent formation of microparticles therefrom.

The steps preliminary to and during formation of microparticles are thus adapted to input sufficient energy so as to form microparticles in the desired size range, which is typically 0.01–10 microns, but not so much energy that DNA is damaged during the process to such an extent that the resultant microparticles are not capable of inducing expression of the polypeptide coded by the DNA. There is a balance required as more vigourous agitation such as through higher mixer speeds typically results in smaller microparticle sizes, and desired sizes are fairly small. But, DNA may be damaged by excessive agitation. On the other hand, reducing the energy input during emulsion formation may have the effect that no emulsion is formed and no microparticles can be obtained. The invention enables a balance of these competing factors, to provide for formation of microparticles retaining an acceptable degree of transducing activity in their encapsulated DNA.

Method steps (a)–(e) may be performed at ambient temperature, which is convenient for laboratory and industrial purposes, and may also be performed at below ambient temperature as this may improve the stability of the plasmid DNA during the encapsulation procedures. The temperature of these steps may optionally be reduced to below 20° C., below 10° C. or even below 5° C. In an embodiment of the invention, steps (a)–(e) of the method is carried out at below ambient temperature using a reduced amount of microparticle precursor compared to the amount used at ambient temperature and then step (f) is carried out at ambient or elevated temperature.

The parameters of the method are thus chosen to promote formation of microparticles of 10 $\mu$m diameter or less, to promote incorporation of DNA into microparticles, and to avoid damage to the DNA such that the resultant microparticles contain functional DNA that can be expressed in the recipient following oral administration.

For any particular choice of polymer and DNA variations in the method may be necessary to obtain best results. The efficiency of a method can be assessed by transformation or transfection assays. In the transformation assay used by the inventors, DNA is recovered from microparticles by dissolution with organic solvent, quantitated and used to transform bacteria-ampicillin selection determines successful transformants. In the transfection assay, recovered DNA is used to transfect eukaryotic cells in culture, which culture is then assayed for presence of the antigen or gene therapy product. These assays have demonstrated that DNA recovered from microparticles produced by the method of the invention can retain 50–60% and up to 80% of the activity of the original DNA, indicating high efficiency of incorporation of functional DNA into microparticles.

The method of the invention is adapted to produce pharmaceutical compositions of the first aspect of the invention. The steps of the method are adapted so that, in a resultant composition which contains many DNA containing polymer particles, a useful proportion of particles contain active DNA, i.e. DNA that has not been damaged by the method such that its ability to induce expression of its coding sequence is lost. DNA activity is measured as a percentage of activity prior to the particle forming step.

An acceptable level of DNA biological activity is at least 10% and preferably at least 25%, though for particularly fragile DNA a lower percentage may be acceptable so long as, in use, a therapeutic effect is obtained using the composition.

In a specific embodiment of the invention, a composition is made by preparing an aqueous solution of a plasmid of double stranded, supercoiled DNA comprising a coding sequence and a eukaryotic promoter. Separately, an organic polymer solution is prepared. The two solutions are mixed together and emulsified at a speed between 1000 and 4000 rpm. A solution of a stabilizing agent is then added and the new mixture emulsified at a speed between 1000 and 4000 rpm. Subsequently, the organic solvent is dispersed or otherwise removed so as to set the polymer into microparticles containing the plasmid DNA, and this step is carried out at 30° C. or higher. After centrifugation and resuspension of particles the DNA within retains 25% or more of its activity.

Accordingly, a second aspect of the invention provides a pharmaceutical composition comprising a plurality of microparticles in a pharmaceutically acceptable carrier, wherein said microparticles are composed of or comprise polymer and contain an aqueous solution of DNA, which DNA comprises a sequence coding for a polypeptide, wherein the composition is adapted to induce expression in a recipient of the polypeptide and wherein the polypeptide is selected from:

(a) the antigens FHA, PT, 68 kd-Pertactin, tetanus toxin, gp48, NS1, Capsid, gp350, NS3, SA, I, NP, E, M, gp340, F, H, HN, 35 kd protein, VP1, E1, E2, C, M, E and MSHA according to table 1; and (b) immunogenic fragments, variants and derivatives of the polypeptides of (a).

Details of Accession numbers of these antigens are listed in table 1 and thus a DNA for incorporation into a microparticle of the invention is prepared following the procedure described in Example 2.

Preferably, the coding sequence is accompanied by a promoter sequence promoting expression of the coding sequence. In embodiments of the pharmaceutical composition for use on mammals, it is convenient to use a eukaryotic promoter and especially a promoter that operates in a wide variety of tissue types. In particular embodiments of the invention, the DNA comprises a tissue- or cell type-specific promoter.

In use, the pharmaceutical composition is orally administered, and the coding sequence is expressed leading to desired therapeutic effects.

A composition of the invention is suitable for vaccination and contains a sequence coding for an immunogen. Following administration of the composition, expressed immunogen elicits production of antibodies within the recipient, thereby contributing to vaccination of the recipient.

Generally, the microparticles of the invention are intended to enter cells of the recipient by phagocytosis, for example phagocytosis by macrophages or other antigen presenting cells. Subsequently, the body of the microparticle breaks down in the intracellular space and the DNA is released. It is preferred that the microparticles of the invention are in the size range 0.01 μm to 30 μm, with 0.1 μm to 10 μm being a more preferred range. These sizes have been found to be suitable for reliably achieving in vivo expression of the DNA. It is also to be noted that agents promoting uptake of the DNA are not needed in microparticles of the invention—as the microparticle size determines its uptake.

Further, where the composition is for oral use, it can conveniently also contain a taste-enhancing agent. The term "taste-enhancing agent" is intended to encompass sweeteners, flavourings and agents that mask any unpleasant taste from other components of the composition. It can conveniently be enterically coated or co-administered with an appropriate antacid formulation.

In a specific embodiment described below, a preparation of microparticles contains a DNA sequence coding for a measles protein. Oral administration of the microparticles elicited an increase in antibodies specific for that protein. Likewise, another microparticle preparation contains a DNA sequence coding for a rotavirus protein. Oral administration of these microparticles preparation elicited anti-rotavirus protein antibodies and a protective effect against challenge by the virus.

The inventors have thus provided DNA encapsulated within a polymer such that the ability of DNA to code for a desired gene product is substantially not affected by the encapsulation process. It is known that DNA can readily be damaged by emulsifying and other steps necessary for production of polymer particles. The inventors have provided for encapsulation of DNA such that sufficient operative DNA is encapsulated for a biological effect to be obtainable upon oral administration of the encapsulated DNA.

The invention offers advantages, in that encapsulated DNA is suitable for oral administration, avoiding the unpleasant and awkward aspects associated with having to inject DNA preparations described in the prior art. Specific embodiments in examples described below have been successful in inducing immunogen-specific antibodies in response to oral administration of a composition of the invention. In addition, the encapsulated DNA formulation is suitable for drying, e.g. freeze drying, into a form that is stable over long periods and is suitable for storage. Further, for many vaccine applications it would be advantageous if, as well as a systemic humoral and cell-mediated immune response, immunity at mucosal surfaces could also be evoked. Specific embodiments of the invention, described below, have been demonstrated to elicit significant increases in specific IgA antibodies, following oral administration. The invention thus provides a pharmaceutical composition comprising DNA within a polymer particle, the DNA encoding a polypeptide, and the composition being adapted to induce mucosal polypeptide specific IgA antibodies in a recipient.

The polymer of the microparticle of the invention preferably is both biodegradable and non-toxic. More preferably, the polymer is suitable for formation of microparticles by a solvent extraction method-for which the polymer should be soluble in an organic solvent so as to form a solution of polymer which will form an water-in-oil emulsion under the conditions described and further solidify around the internal water droplet when the solvent is extracted from the (water-in-oil)-in-water double emulsion.

Suitable polymers include lactide containing polymers and glycolide containing polymers and copolymers of 0–100:100–0 lactide:glycolide. In a specific embodiment of the invention, the polymer comprises poly (DL-lactide-co-glycolide), otherwise referred to as PLG, chosen as it has been approved for human and veterinary use.

The products of the invention are typically for in vivo use vaccination of animals, in particular humans. The polymer of the microparticle should therefore be non toxic in vivo and suitable for pharmaceutical use. The polymer should further be biodegradable—either by consisting of or comprising biodegradable polymer—so that it releases its DNA in the recipient. There exists in the art an extensive literature on polymers suitable for human and animal use. In this connection, the disclosures of EP-A-0451390, WO-A-95/31184 and WO-A-95/31187 are incorporated herein by reference.

The DNA contained within the particle will typically comprise double stranded DNA. The construction of a suitable DNA sequence for use in the invention will be appreciated by persons of skill in the art. It is preferred that the sequence comprises both a transcriptional promoter and a gene coding sequence. It is further preferred that the DNA sequence provides for transcription termination and polyadenylation downstream of the coding sequence.

It is particularly preferred that the DNA be double stranded, circular and super coiled or coiled to some extent. It has been observed that during manufacture of microparticles the DNA is subjected to severe shear forces. Using particular particle manufacturing conditions, the inventors have managed to retain functional DNA, though have observed that previously supercoiled DNA may become partly converted to the open circular form in the process.

Plasmid DNA or DNA derived therefrom by conventional manipulations is particularly suitable and is used in the specific embodiments of the invention described below. As there is extensive literature relating to plasmid manufacture a person of skill in the art will readily be able to prepared a plasmid suitable for the microparticle of the invention. In general, plasmids incorporating any eukaryotic promoter sequence are suitable.

A further optional feature of the invention is that DNA-containing polymer particles can be manufactured so as to have different half-lives in vivo. When administering an antigen during vaccination, it may be advantageous for the antigen to be delivered in two distinct time frames, such as an initial short term dose followed by a slower, long term dose over a long time frame. A particular embodiment of the invention provides a vaccine comprising first and second vaccine components, the first vaccine component comprising polymer-encapsulated DNA wherein the DNA includes a sequence coding for an immunogen and wherein the polymer has a first half life in vivo, and a second vaccine component comprising polymer encapsulated DNA, wherein the DNA contains a sequence coding for an immunogen and wherein the polymer has a second half-life in vivo. The respective half-lives could be up to 5 days and more than 5 days. In one example, the immunogen of the first and second vaccine components are the same. Alternatively, the respective vaccine components can contain DNA sequences coding for different immunogens.

In an embodiment of the invention, the half-lives of the respective first and second vaccine components are up to two days, and more than two weeks. In a further embodiment, the first and second half-lives differ by at least an order of magnitude.

A third aspect of the invention provides a pharmaceutical composition comprising polymer-encapsulated DNA and having a reduced water content, such as less than 5% by weight. This composition is suitable for long term storage while retaining the ability of the DNA, upon administration to a recipient, to induce expression of a coding sequence within said DNA.

A method of preparing a pharmaceutical composition for storage, is to dry, such as by freeze drying, a pharmaceutical composition according to the first aspect of the invention. It is preferred that the dried composition has a water content of less than 5%, though the precise water content will be determined by the period of drying used.

A fourth aspect of the invention provides a method of vaccination comprising administering a vaccine according to the first aspect of the invention. Vaccination can thus be obtained by eliciting antibodies to the immunogen expressed from the gene coding sequence. As will be appreciated, the immunogen can be a component of a virus or bacterium or other pathogenic microorganism, or can be an analogue of said immunogen such that antibodies against the analogue are effective against the pathogen itself.

According to a fifth aspect of the invention there is provided use of a microparticle according to the first aspect of the invention in manufacture of a medicament for inducing production of IgA antibodies.

In a specific embodiment of the invention described in an example below, the particle material is PLG. The size of particles produced by the method of the invention are generally in the range of 0.01–30 μm, preferably 1–10 μm. Other suitable polymer formulations for DNA-containing particles according to the present invention include polylactic acid, poly-hydroxybutyrate, poly hydroxyvalerate, poly (hydroxybutrate/valerate), ethyl cellulose, dextran, polysaccharides, polyalkylcyanoacrylate, poly-methyl-methacrylate, poly(e-caprolactone) and mixtures of all of these components.

As will be appreciated by a person of skill in the art, a wide range of DNA sequences and constructs are suitable for use in this invention. In particular, the invention can be practised incorporating a wide range of plasmid vectors already well known and characterised in the art. Typically, a plasmid vector used in this invention will include a cDNA that codes for the desired gene product. The selection of additional components for the DNA sequence, such as promoters, reporter genes and transcription termination sequences can be made by a person of skill in the art according to common general knowledge concerning construction of known plasmid vectors.

The preferred administration route for compositions of the invention is the oral route, meaning that compositions of the invention should preferably be designed to avoid significant degradation while passing through the stomach with its high acid levels. It is known that uptake of microparticles of less than 10 μm in size occurs, inter alia, in the M cells of the intestine, and thus inclusion of DNA containing particles in this size range can be advantageous in promoting uptake at this intestinal location. Other modifications to the nature and character and components of the polymer can be made within the concept of the invention.

BRIEF DESCRIPTION OF THE DRAWINGS

There now follows description of specific embodiments of the invention, accompanied by figures in which.

EXAMPLES

Example 1

Method for Encapsulation of Plasmid DNA in PLG Microparticles

Equipment:

1) Silverson Laboratory mixer with ¾" probe fitted with emulsor screen.
2) High speed centrifuge.
3) Normal laboratory glassware, beakers, measuring cylinders, stirrers etc.

Reagents:

1) Poly(lactide-co-glycolide) (PLG) solution—500 mgs in 3 ml dichloromethane.
2) Plasmid DNA (12 mg/ml in water).
3) Polyvinyl alcohol (PVA) solution (8% w/v in water).
4) Absolute ethanol.
5) TEN buffer (10 mM tris pH 8.0+1 mM EDTA+50 mM NaCl).

Method:

1) Mix 200 μl plasmid DNA solution with 250 μl of TEN and add 150 μl ethanol with stirring. Mix well.
2) Add this mixture to 3 ml PLG solution and emulsify in the Silverson mixer at 3000 rpm for 2 min.
3) Add this emulsion to 100 ml PVA and emulsify at 3000 rpm for 2 min.
4) Add the double emulsion to 1 liter of water and stir vigorously for 1 min.
5) Distribute the suspension of microparticles in centrifuge containers and centrifuge at 10,000×$g_{av}$ for 30 mins.
6) Resuspend the microparticle pellet in 25 ml of water and homogenise with a hand homogeniser with large clearance (0.5 mm) to make a homogeneous suspension. Dilute with 200 ml of water and recentrifuge as above.
7) Repeat step 6 three times.
8) Resuspend the microparticle pellet in 25 ml of water as above, transfer to a vessel suitable for freeze drying, shell freeze in an isopropanol/dry ice mixture and lyophilise for 48 h.

In this method, steps 1–3 are carried out at ambient temperature. DNA was incorporated into the microparticles with an efficiency of about 25%.

Example 2

Plasmids for the Expression of Proteins after in vivo Delivery

Figure 1:
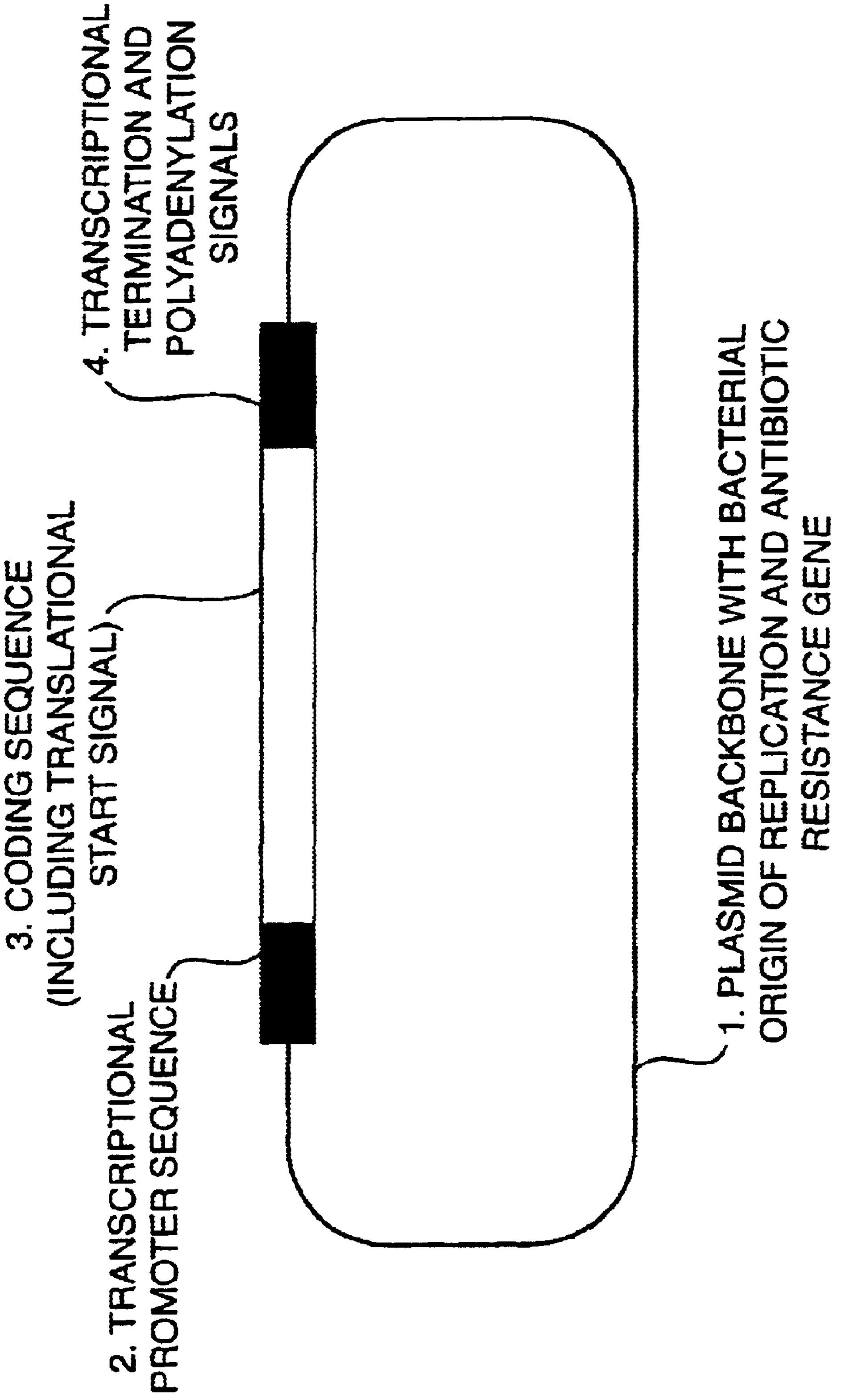
FIG. 1 is a schematic diagram of the components of a protein-expressing plasmid suitable for incorporation into a DNA-containing particle according to the invention.

Suitable plasmids for use in microparticles according to the invention consist of the following components (see FIG. 1):

1. Plasmid Backbone The plasmid backbone has an origin of replication and an antibiotic resistance gene or other selectable marker to allow maintenance of the plasmid in its bacterial host. Backbones providing a high copy number will facilitate production of plasmid DNA. An example would be from the pUC plasmid vectors.
2. Transcriptional Promoter Sequence Expression of the desired protein will be driven by a, typically eukaryotic, transcriptional promoter initiating the synthesis of mRNA. Generally, strong promoters functioning in a wide variety of tissue types and animal species are to be used, e.g. the human cytomegalovirus immediate early (hCMV IE) promoter. However, particularly for gene therapy applications, a tissue or cell type-specific promoter may be more appropriate.
3. Coding Sequence The coding sequence contains the DNA sequence encoding the protein of interest. It contains the translational start codon ATG in sequence context favourable for initiation of protein synthesis. The coding sequence ends with a translational termination codon. Proteins to be expressed include a) reporter enzymes (e.g. luciferase, β-galactosidase); b) components of pathogenic microorganisms capable of inducing protective immune responses (e.g. the NS1 protein of tick-borne encephalitis virus, the N, H or F proteins of measles virus, the gp120 protein of human immunodeficiency virus 1); c) enzymes or other proteins intended for the treatment of genetic disease (e.g. glucocerebrosidase for the treatment of Gaucher's disease).
4. Transcription Termination Sequence Improved expression levels are obtained under some circumstances when sequences causing termination of mRNA transcription are incorporated downstream of the coding sequence. These sequences frequently also contain signals causing the addition of a poly A tail to the mRNA transcript. Sequences which can be used in this role can be derived from the hCMV major immediate early protein gene or from SV40 viral DNA or elsewhere.

Example 3

We have constructed a plasmid encoding the insect protein luciferase, under the transcriptional control of the human cytomegalovirus immediate early (hCMV IE) promoter, and demonstrated luciferase activity in cells transfected in vitro.

We encapsulated purified plasmid DNA in PLG microparticles around 2 μm in size with moderate (about 25%) efficiency using the protocol of Example 1. Agarose gel electrophoresis indicates that a proportion of the initially closed circular supercoiled DNA undergoes conversion to a more slowly migrating form, probably relaxed circles, as a result of shear stresses in the encapsulation process. The encapsulated DNA was released from the particles and shown to retain a significant fraction of its in vivo biological activity in assays of bacterial transformation by electroporation, and luciferase expression after transfection into cultured cells. Microencapsulated DNA (50 μg) was administered to mice by intraperitoneal (i.p.) injection and orally. Control animals received unencapsulated DNA by the same routes, and as a positive control by standard intramuscular (i.m.) injection. Luciferase-specific serum antibodies were analyzed by ELISA three and six weeks after DNA administration. Results are presented in FIG. 2.

Figure 2:
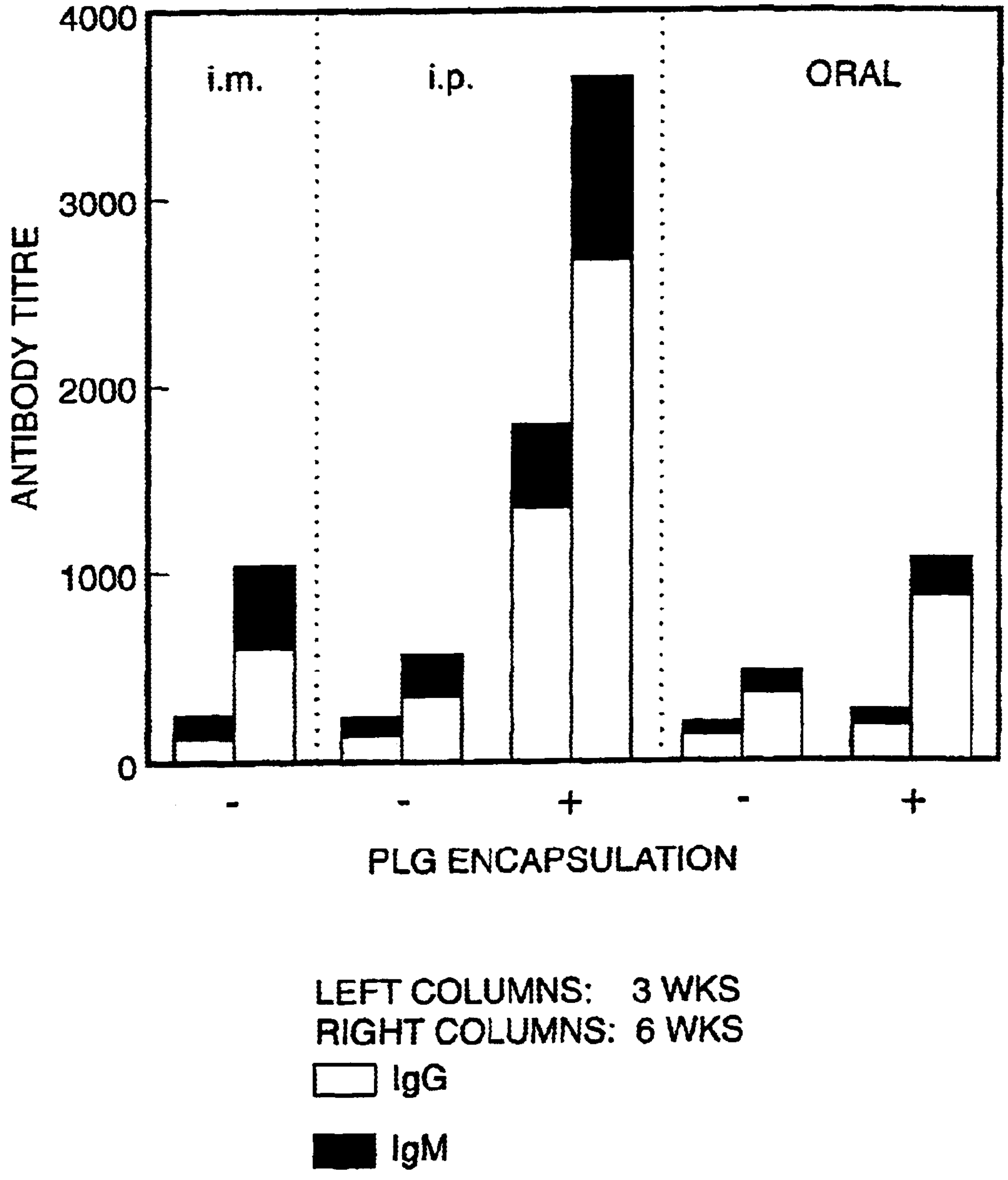
FIG. 2 illustrates the results of example 3, namely induction of luciferase-specific serum antibodies by PLG-encapsulated plasmid DNA, and in which the left column indicates antibody titre after 3 weeks and the right column indicates antibody titre after 6 weeks (i.m. represents intra muscular, i.p. represents intra peritoneal, the bottom portion of each column represents IgG levels, the top portion represents IgM levels)

As shown in FIG. 2, modest specific IgG and IgM responses were seen after i.m. injection, as might be expected. Encapsulated DNA evoked strong IgG and IgM responses after i.p. injection, while unencapsulated DNA gave much weaker responses. Similarly, orally administered encapsulated DNA evoked a good IgG response which was not matched by unencapsulated DNA. The IgG and IgM antibody responses indicate that luciferase expression and presentation to the immune system occur after administration of plasmid DNA encapsulated in PLG microparticles with efficiencies exceeding that seen with the standard i.m. route, and exceeding that seen in comparative administration of unencapsulated DNA.

Example 4

In further experiments, microencapsulated DNA, made by the method of Example 1, in a range of doses (1–50 μg DNA) was administered to groups of outbred mice by intra-peritoneal (i.p.) injection or orally. Luciferase-specific serum antibodies of IgG, IgM and IgA classes were analysed by ELISA at 3,6 and 9 weeks after DNA administration.

Figure 3:
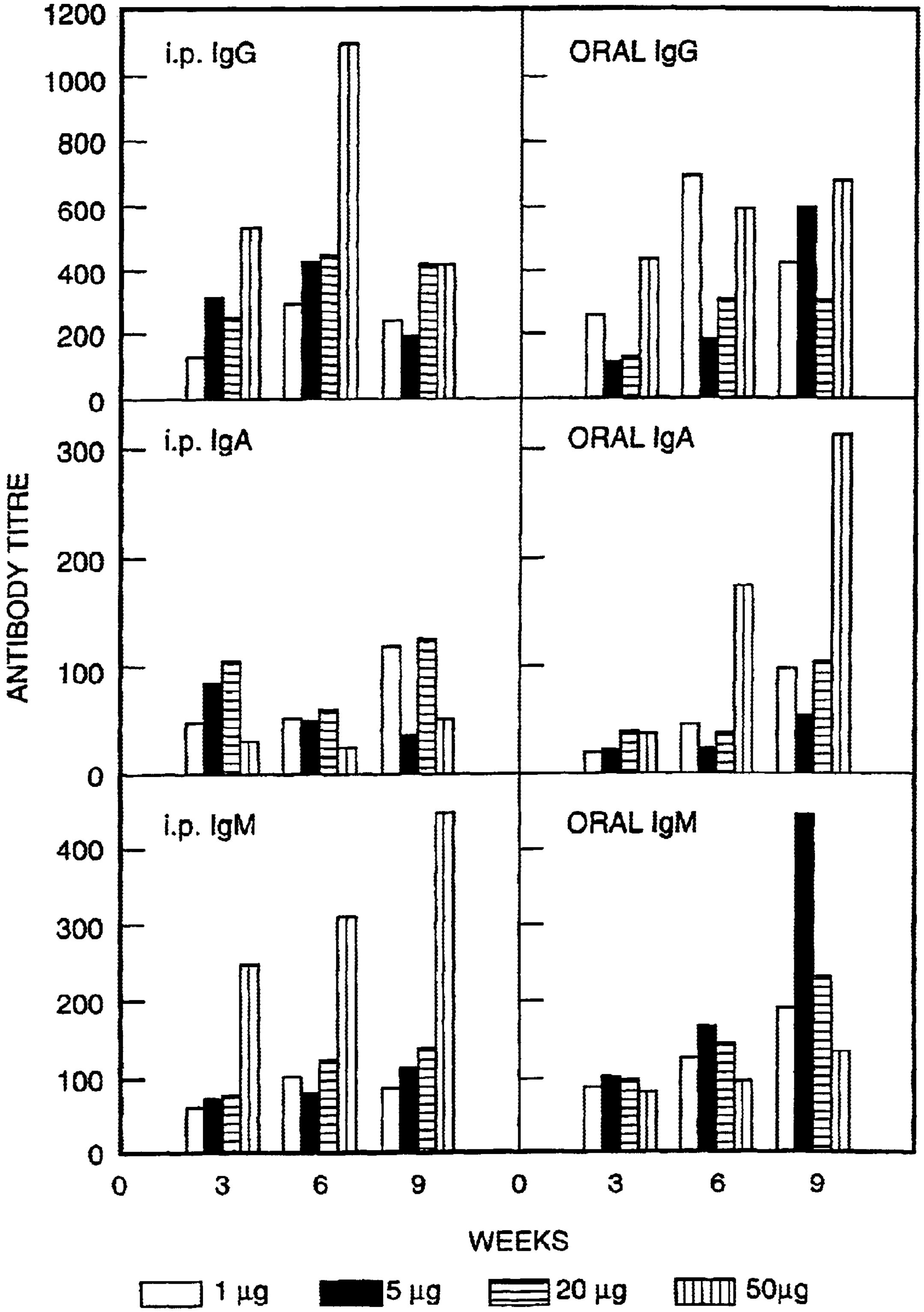
FIG. 3 shows dose-response data for injected and oral doses of encapsulated DNA, with the titre of IgG, IgM and IgA in each case.

In FIG. 3, it can be seen that i.p. injection of PLG-encapsulated DNA evoked good IgG and IgM responses, and a modest IgA response. Orally administered encapsulated DNA evoked good responses in all three antibody classes. There is a trend for the antibody titres to increase with time after DNA administration, and the responses are also dose-related to a greater or lesser extent. It is apparent that quantities of DNA as low as 1 μg are able to evoke significant responses, especially at longer times after administration. These antibody responses again confirm that luciferase expression occurs after administration of plasmid DNA encapsulated in PLG microparticles, either by i.p. injection or orally. They also demonstrate that antigen is presented to the immune system by these means in such a fashion as to evoke IgG, IgM and IgA classes of antibody.

Example 5

We examined the effect of high-speed homogenisation steps, used to generate the required water-oil-water emulsions which are intermediates in the encapsulation process, on the physical integrity and biological function of plasmid DNA.

Figure 4A:
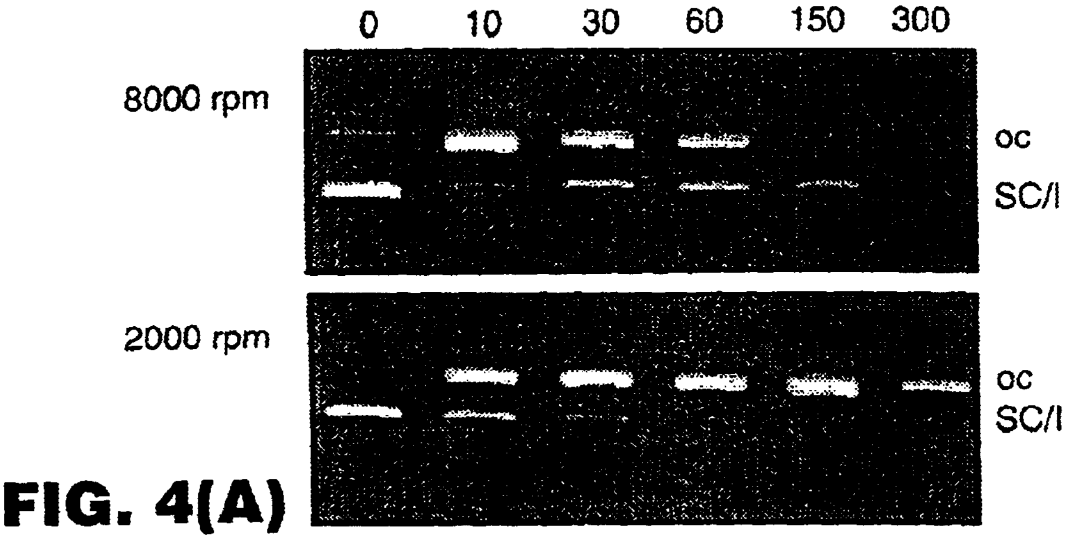
FIG. 4 shows: A—agarose gel electrophoresis of plasmid DNA following homogenisation in a Silverson mixer at 2000 and 8000 rpm for 0–300 seconds; and B—agarose gel electrophoresis of DNA before and after encapsulation.

In initial experiments, supercoiled plasmid DNA was adjusted to concentrations and volumes similar to those to be used in microencapsulation experiments, and homogenised with a Silverson laboratory homogeniser. Samples were removed at intervals from 0 to 300 sec for analysis by agarose gel electrophoresis (FIG. 4A). Such an analytical procedure is capable of distinguishing between supercoiled (sc) DNA, open circular (oc) DNA, where a single strand has been nicked, and linear (I) DNA, where both strands have been cut at adjacent points (see, for example, FIG. 2C in Garner and Chrambach 1992. Resolution of circular, nicked and linear DNA, 4.4 kb in length, by electrophoresis in polyacrylamide solutions. *Electrophoresis* 13, 176–178). It is clear that exposure to such conditions for periods as short as 10 sec results in conversion from sc to oc form. At 8000 rpm, further conversion to the linear form and eventually more extensive degradation occur. However, at the reduced speed of 2000 rpm the oc form of DNA is relatively stable over the time period typically required for formation of the emulsion intermediates involved in PLG encapsulation. These studies thus show that plasmid DNA is vulnerable to shear-induced damage, and careful attention is required to the precise conditions to obtain encapsulation of minimally altered DNA.

Figure 4B:
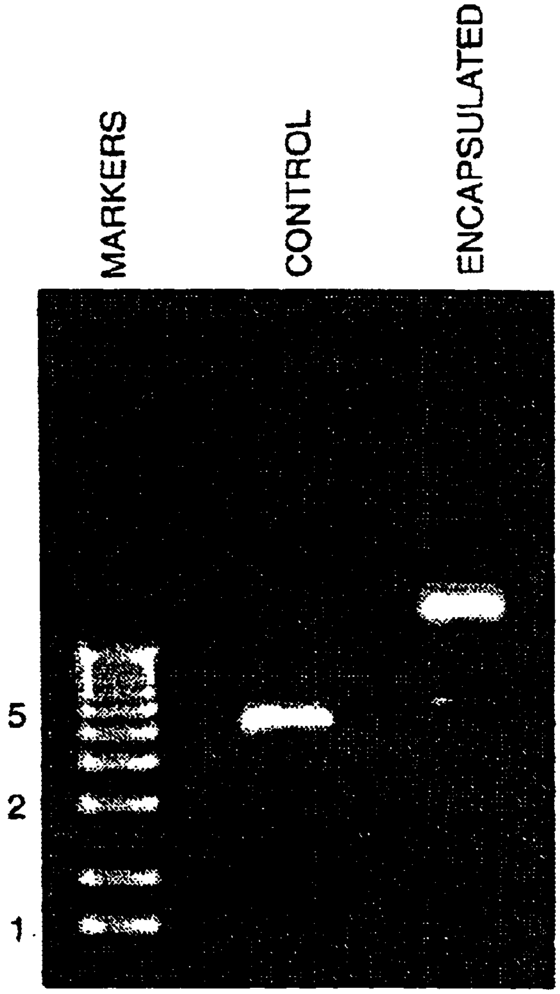

From this basis, we have developed conditions for the encapsulation of purified plasmid DNA in PLG microparticles around 2 μm in size with moderate (about 25%) efficiency. Agarose gel electrophoresis (FIG. 4B) indicates that the initially closed circular supercoiled DNA undergoes conversion to the oc form, as a result of shear stresses in the encapsulation process. Biological activity of DNA released from microparticles has been assessed in assays of bacterial transformation by electroporation, and luciferase expression after transfection into cultured cells. DNA released from the particles retains a significant fraction (about 25%) of its in vitro activity in both these assays.

Example 6

Figure 5:
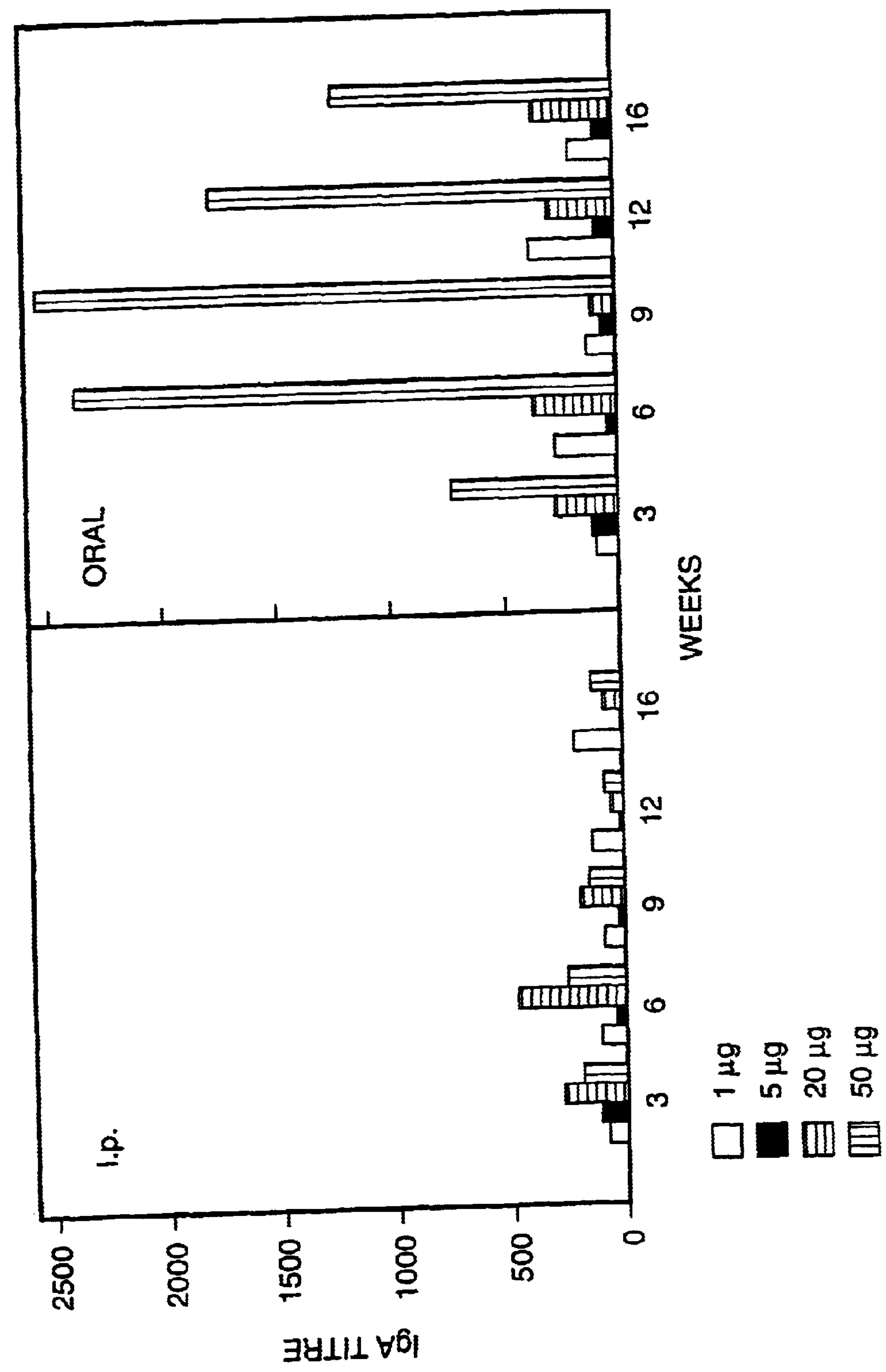
FIG. 5 shows stool anti-luciferase IgA response to DNA within PLG microparticles.

PLG-encapsulated DNA coding for luciferase, made by the method of Example 3, is also able to evoke a mucosal immune response to the expressed protein. Levels of IgG, IgM and IgA antibodies specific for luciferase were assessed by ELISA in stool samples from mice which received i.p. or oral doses of 1, 5, 20 or 50 μg of PLG-encapsulated DNA. No significant levels of IgG or IgM antibodies were found in stool samples from any group of mice. Rather limited IgA responses were seen in the i.p.-injected mice; however, oral administration resulted in significant levels of luciferase-specific IgA antibodies in the stool samples (FIG. 5). These reached extraordinarily high levels in those mice which received 50 μg PLG-encapsulated DNA. These results indicate that oral administration of a single dose of PLG encapsulated plasmid DNA is capable of evoking a mucosal, as well as a systemic antibody response. This may be a useful attribute of a PLG-encapsulated DNA vaccine in applications where protection against infection at mucosal surfaces is desirable, as for measles or AIDS.

Example 7

We have exploited a plasmid expressing the measles virus (MV) nucleocapsid protein (N) to extend our observations that the oral administration of encapsulated plasmid DNA expressing luciferase is capable of eliciting a systemic antibody response. The N-expressing construct is identical to that expressing luciferase (described in example 3), except for the replacement of the coding sequence with the Edmonston strain MV N coding sequence. The purified plasmid DNA was PLG-encapsulated (using the method as described in example 1).

Figure 6B:
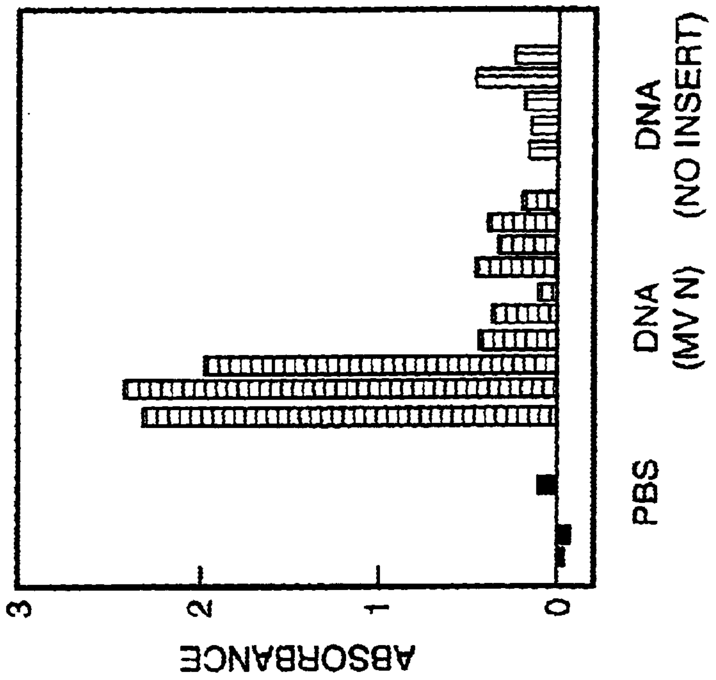
FIG. 6 shows the results of oral administration of PLG-encapsulated DNA expressing measles virus N protein.
Figure 6A:
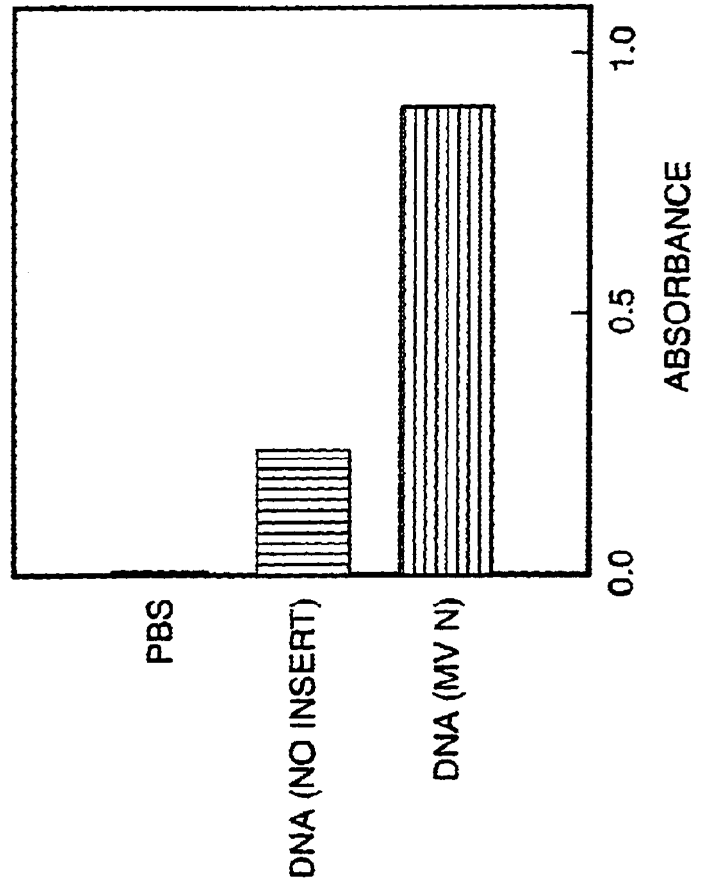

Inbred C3H mice were immunized with two doses suspended in 0.1 M Sodium bicarbonate administered by oral gavage, 13 days apart; each dose contained 50 μg DNA. Control groups of mice received PBS alone or PLG particles containing plasmid vector DNA containing no coding sequence. Mice were bled at intervals and serum levels of IgG specific for MV N determined by ELISA, using recombinant MV N expressed in insect cells as antigen. As shown in FIG. 6A, immunization with PLG-encapsulated DNA expressing MV N resulted in significant levels of N-specific antibody; results shown are mean absorbances in 1/100 diluted sera taken 53 days after the second DNA administration. There seems to be a considerable degree of variability in the response of individual mice to DNA immunization in these experiments (see FIG. 6B), but very high levels of antibody (reciprocal titres exceeding $10^4$, determined in follow-up experiments) are present in some animals. These results demonstrate that oral delivery of PLG-encapsulated DNA is an effective method for inducing an immune response against an important pathogen.

Example 8

A Further Method for Encapsulation of Plasmid DNA in PLG Microparticles

Equipment:

1) Silverson Laboratory mixer with ¾" probe fitted with emulsor screen.
2) High speed centrifuge.
3) Normal laboratory glassware, beakers, measuring cylinders, stirrers etc.

Reagents:

1) Poly(lactide-co-glycolide) (PLG) solution—500 mgs in 3 ml dichloromethane.
2) Plasmid DNA (>10 mg/ml in TE buffer).
3) Polyvinyl alcohol (PVA) solution (8% w/v in water).
4) Absolute ethanol.
5) TE buffer (10 mM tris pH 8.0+1 mM EDTA+50 mM NaCl).

Method:

1) Mix 450 μl plasmid DNA solution with 150 μl ethanol with stirring. Mix well.
2) Add this mixture to 3 ml PLG solution and emulsify in the Silverson mixer at 2000 rpm for 2½ min.
3) Add this emulsion to 100 ml PVA and emulsify at 2000 rpm for 2½ min.

4) Add the double emulsion to 1 liter of water and stir vigorously for 1 min.

5) Distribute the suspension of microparticles in centrifuge containers and centrifuge at 10,000×$g_{av}$ for 30 mins.

6) Resuspend the microparticle pellet in 25 ml of water and homogenise with a hand homogeniser with large clearance (0.5 mm) to make a homogeneous suspension. Dilute with 200 ml of water and recentrifuge as above.

7) Repeat steps 5 and 6 four times.

8) Resuspend the microparticle pellet in 25 ml of water as above, transfer to a vessel suitable for freeze drying, shell freeze in an isopropanol/dry ice mixture and lyophilise for 48 h.

In this method, steps 1–3 are carried out at ambient temperature. The efficiency was improved compared to example 1, up to 30–40% efficiency.

Example 9

A Further Method for Encapsulation of Plasmid DNA in PLG Microparticles

Equipment:

1) Silverson Laboratory mixer with ¾" probe fitted with emulsor screen.

2) High speed centrifuge.

3) Normal laboratory glassware, beakers, measuring cylinders, stirrers etc.

Reagents:

1) Poly(lactide-co-glycolide) (PLG) solution—400 mgs in 3 ml dichloromethane.

2) Plasmid DNA (>10 mg/ml in TE buffer).

3) Polyvinyl alcohol (PVA) solution (8% w/v in water).

4) Absolute ethanol.

5) TE buffer (10 mM tris pH 8.0+1 mM EDTA.

Method:

1) Mix 450 μl plasmid DNA solution with 150 μl ethanol with stirring. Mix well.

2) Add this mixture to 3 ml PLG solution and emulsify in the Silverson mixer at 2000 rpm for 2½ min.

3) Add this emulsion to 100 ml PVA and emulsify at 2000 rpm for 2½ min.

4) Add the double emulsion to 1 liter of water and stir vigorously for 1 min.

5) Distribute the suspension of microparticles in centrifuge containers and centrifuge at 10,000×$g_{av}$ for 30 mins.

6) Resuspend the microparticle pellet in 25 ml of water and homogenise with a hand homogeniser with large clearance (0.5 mm) to make a homogeneous suspension. Dilute with 200 ml of water and recentrifuge as above.

7) Repeat steps 5 and 6 four times.

8) Resuspend the microparticle pellet in 25 ml of water as above, transfer to a vessel suitable for freeze drying, shell freeze and lyophilise for 48 h.

In this method, steps 1–3 are carried out at 4° C. The efficiency of incorporation of DNA into microparticles was 50–60%.

Example 10

Plasmid DNA (pCMVIA/VP6) expressing the VP6 gene of murine rotavirus (epizootic diarrhoea of infant mice (EDIM) virus) was constructed at the University of Massachusetts Medical Center. The gene encoding VP6 was inserted into a vector (pJW4303) downstream of sequences of the immediate early transcriptional promoter and intron A of human cytomegalovirus and a tPA-derived secretory signal sequence. The gene was followed by transcriptional termination and polyadenylation sequences derived from the bovine growth hormone gene. The purified plasmid DNA was PLG-encapsulated using the method described in example 1.

Inbred Balb/c mice were immunized by oral administration with a dose containing 50 micrograms VP6-expressing DNA encapsulated in PLG microparticles. A control group of mice received a similar dose of encapsulated vector DNA. Mice were examined for intestinal rotavirus-specific IgA at fortnightly intervals by ELISA, using EDIM virus as antigen. Nine weeks after immunisation, the animals were challenged with EDIM virus, and monitored for excretion of virus in stool using a monoclonal antibody-based ELISA.

Figure 7B:
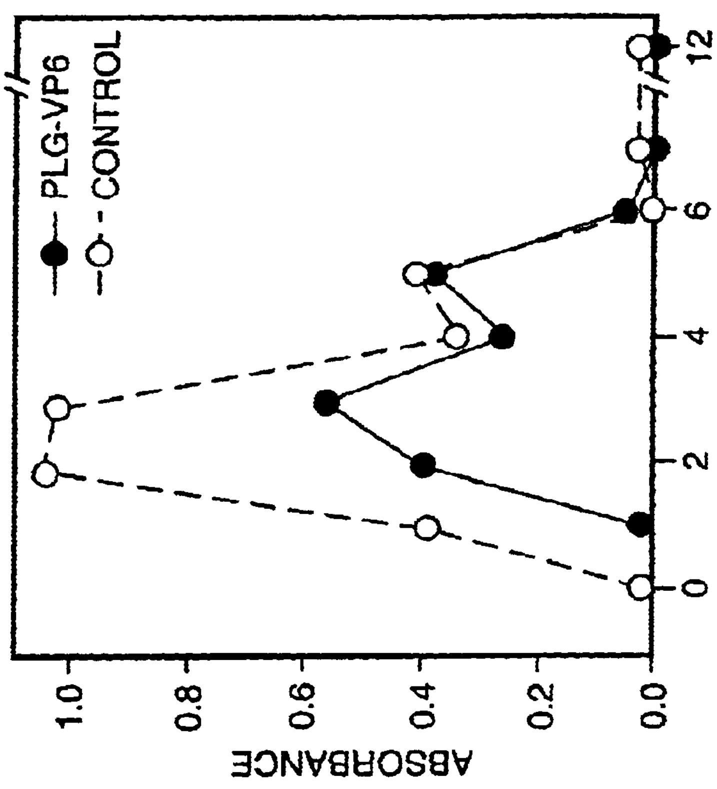
FIG. 7 shows the results of oral administration of PLG-encapsulated DNA expressing rotavirus VP6 gene: A—faecal rotavirus-specific IgA response, B—rotavirus shedding after challenge of orally immunized mice.
Figure 7A:
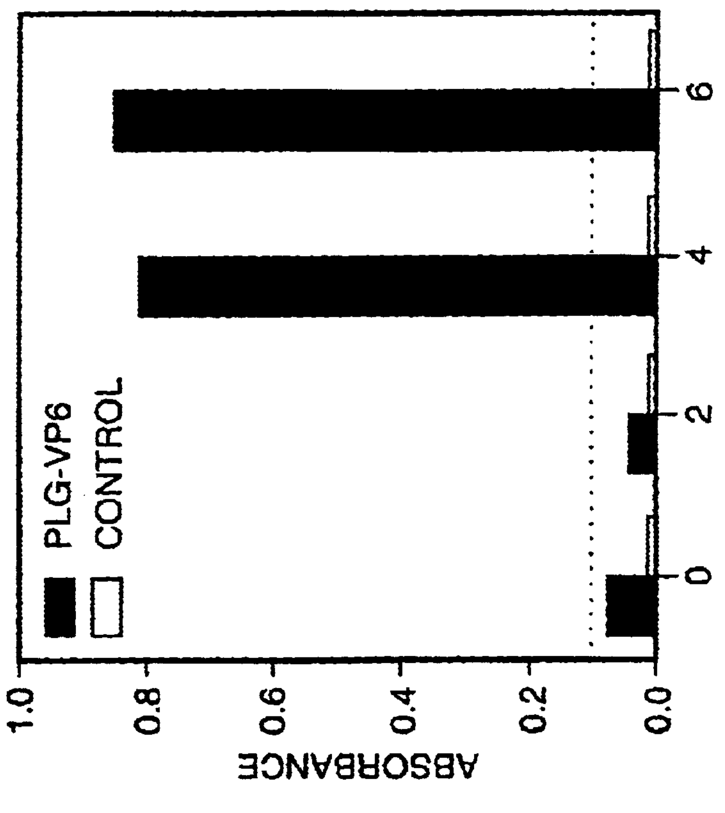

As shown in FIG. 7A, immunisation with PLG-encapsulated DNA expressing VP6 resulted in significant levels of rotavirus-specific intestinal IgA antibody when compared with the control animals. This is particularly noteworthy, since other routes of administration of VP6-expressing plasmid DNA do not elicit detectable levels of intestinal virus-specific IgA before virus challenge. After challenge with EDIM virus, there was a reduction in rotavirus shedding in mice which had received PLG encapsulated VP6-expressing plasmid DNA, compared with the control group (FIG. 7B).

These results demonstrate that orally administered PLG-encapsulated plasmid DNA is capable of inducing a) a specific intestinal IgA response, and b) protection against virus challenge, as manifested in a reduction in virus shedding.

Example 11

We have demonstrated protection against a lethal challenge of mice with measles following oral immunisation with a microencapsulated plasmid DNA encoding the measles nucleocapsid (N) protein plasmid pMV64 (Fooks, A. R., Stephenson, J. R., Warnes, A., Dowsett, B., Rima, B. K. and Wilkinson, G. W. G. (1993). Measles virus nucleocapsid protein expressed in insect cells assembles into nucleocapsid-like structures. J. Gen. Virol. 74 :1439–1444, and Fooks, A. R., Schadeck, E., Liebert, U. G., Dowsett, B., Rima, B. K., Steward, M., Stephenson, J. R. and Wilkinson, G. W. G. (1995). High-level expression of the measles virus nucleocapsid protein by using a replication-deficient Adenovirus vector: Induction of an MHC-1-restricted CTL response and protection in a murine model. Virology. 210: 456–465).

Seven day old C3H/He mice were deprived of food and water for 6 hours immediately prior to immunisation by oral gavage. Each animal received a single dose of 100 μg of pMV64 encapsulated in PLG microspheres suspended in 0.1M sodium bicarbonate. Control animals received an equivalent dose of pMV100 plasmid vector or PBS alone by the same route. Mice were challenged 16 days post immunisation by intracranial injection with $10^5$ pfu/mouse of a neurovirulent rodent-adapted strain of measles (CAM/RB). The survivors in the immunised group compared to the those in the control groups are shown in FIG. 8.

Figure 8:
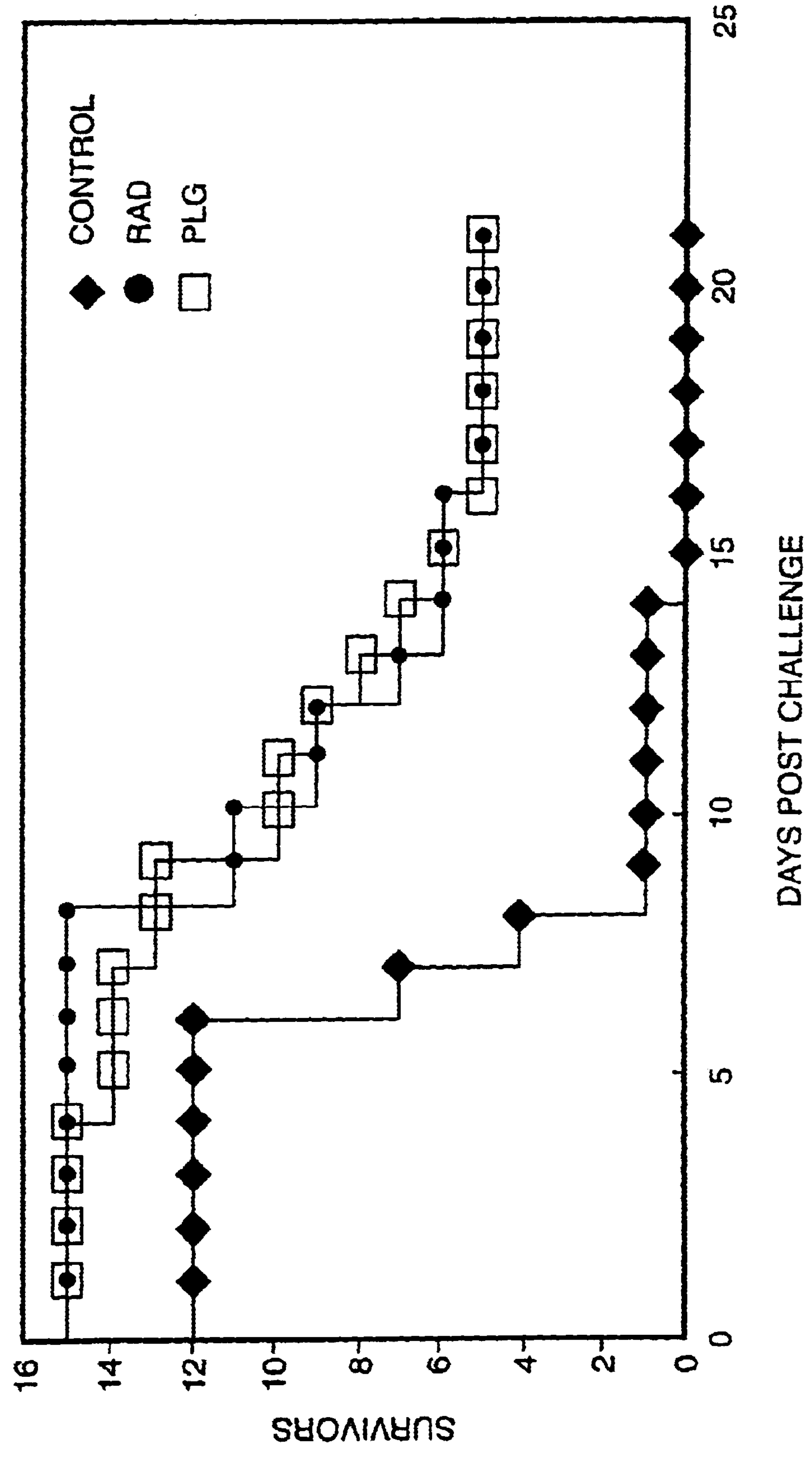
FIG. 8 shows animal protection data showing the protection of mice from measles virus challenge after oral immunisation with PLG encapsulated pDNA encoding the measles N protein (y axis-survivors, x axis-days post challenge)

As evident from FIG. 8 significant numbers of mice immunised with encapsulated pMV64 given by the oral route are able to withstand the lethal effects of the live virus challenge long after the control animals had died. Protection against infection of baby mice with measles virus, as demonstrated in this example, is believed to be mediated by Th1 responses (Reich, A., Erlwien, O., Niewiesk, S., Ter Meulen, V. and Liebert, U. G. (1992). CD4+T cells control measles virus infection of the central nervous system. Immunology 76: 185–191, and Niewiesk, S. Brinckmann, U., Bankamp, B., Sirak S., Liebert, U. G and Ter Meulen, V. (1993). Susceptibility to measles virus-induced encephalitis in mice correlates with impaired antigen presentation to cytotoxic T lymphocytes. J. Virol. 67: 75–81), and thus our results suggest that orally delivered encapsulated pDNA does stimulate cellular immunity.

Example 12

Orally delivered microencapsulated plasmid DNA has been assessed for the induction of cellular immunity, which is known to play an important role in control and elimination of infections.

Groups of mice were given a single dose (50 μg) of encapsulated plasmid encoding the luciferase gene (Example 3) by the intraperitoneal (i.p.), sub-cutaneous (sub. cut.) or oral routes. A fourth group of animals were given 50 μg of 'naked' plasmid DNA by direct injection intra muscularly (i.m.). Sixteen weeks after immunisation animals were sacrificed when spleens and mesenteric lymph nodes (MLN) were removed. After gentle homogenisation, lymphocytes from these tissues were prepared using density gradient centrifugation (LymphoPrep.™). Cells were washed in serum free medium, counted and resuspended to a final concentration of $5\times10^6$ viable cells/ml in an appropriate complete culture medium supplemented with antibiotics. Aliquots of cells (100 μl) were dispensed into individual wells of a 96 well flat bottomed microtitre plate containing either positive control mitogens—concanavalin A, anti-CD3 antibody or a combination of anti-CD3 antibody and phorbol ester (to establish levels of cell viability and to determine maximum incorporation rate) or luciferase antigen (20 μg/ml) to determine antigen specific cell stimulation. Negative controls wells contained cells in medium alone. The incorporation of $^3$H-thymidine into proliferating cells harvested from cultures after 4 days incubation at 37° C., was measured by scintillation. A stimulation index was calculated as the ratio of the mean counts per minute (stimulated cells) to the mean counts per minute (control cultures).

Figure 9:
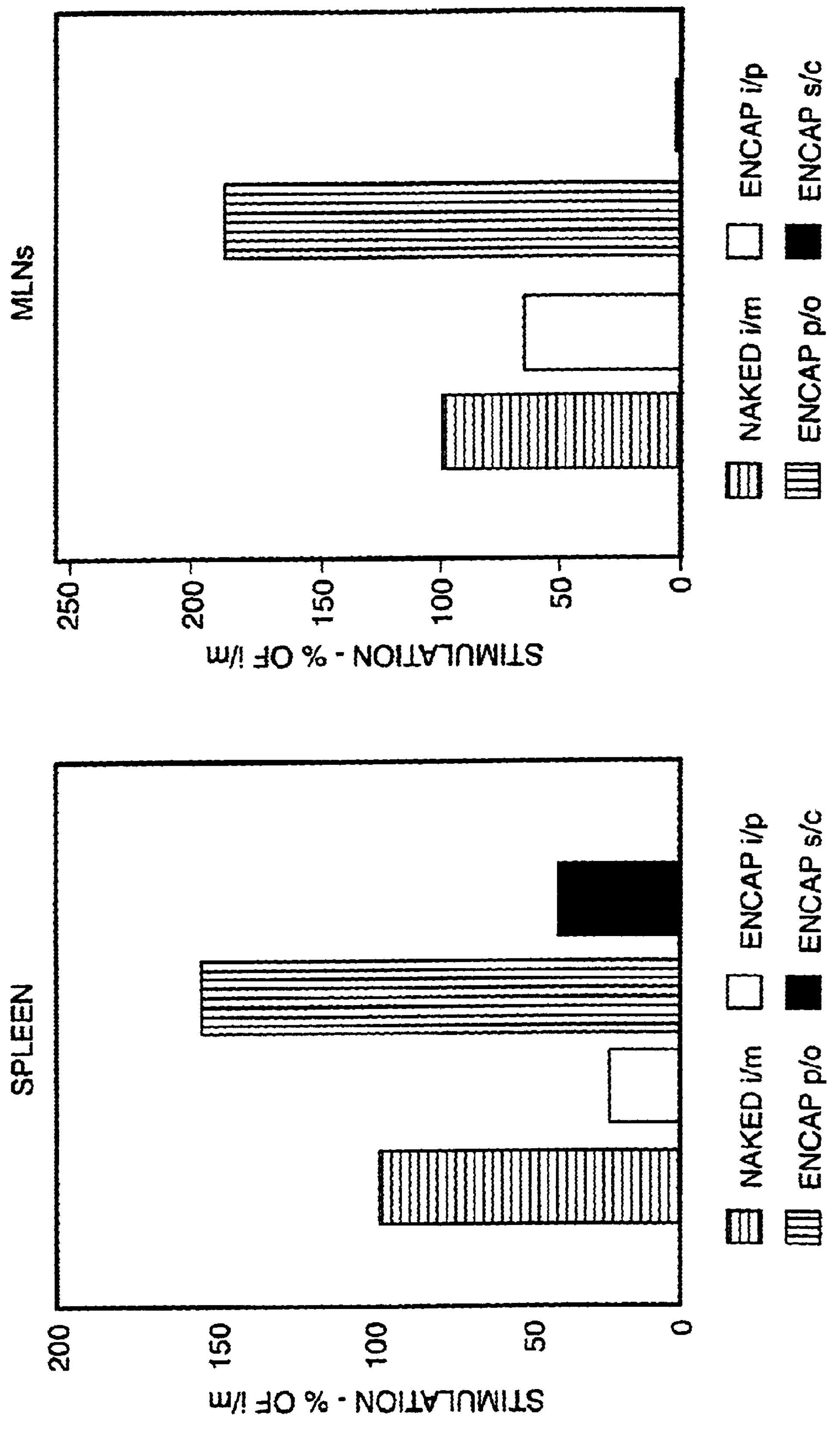
FIG. 9 shows lymphoproliferation in splenocytes and MLNs.

FIG. 9 shows the stimulation indexes obtained from populations of spleen cells and mesenteric lymph node cells in animals immunised with a single dose comprising 50 μg of luciferase coding plasmid A clear and significant stimulation of spleen derived lymphocytes is evident after sixteen weeks post immunisation illustrating that orally delivered encapsulated plasmid DNA is more effective at stimulating systemic Th1 responses than direct injection into muscle. Although not as obvious, a trend in the luciferase specific stimulation of lymphocytes derived from the MLN tissue in the orally immunised animal group is also evident, suggesting that this delivery system is capable of inducing a specific mucosal cellular immune response. At the time of application these two examples were the first clear demonstration of cellular immunity and, importantly mucosal cellular immunity, elicited by encapsulated DNA given by the oral route.

Example 13

We have extended our initial observations that the oral delivery of microencapsulated plasmids encoding rotavirus genes can elicit intestinal immunity and a significant degree of protection against rotavirus infection. Plasmid DNA (pCMVIA/VP6) encoding the VP6 gene of a murine rotavirus, which causes epizootic diarrhoea in infant mice, has been constructed by the University of Massachusetts Medical Centre. (Herrmann, J. E., Chen, S. C., Fynan, E. F., Santoro, J. C. Greenberg, H. B., Wang, S. and Robinson H. L. (1996). Protection against rotavirus infections by DNA vaccination. J. Infect. Dis. 174: S93–97). The plasmid was encapsulated in PLG microspheres using the modifications of Example 1 described in Example 10 herein.

Groups of mice were immunised orally (by gavage) with a single dose of plasmid pCMVIA/VP6 (approx. 50 μg Plasmid DNA per mouse) encapsulated in PLG microspheres. Animals in control groups were given equivalent amounts of a microencapsulated empty plasmid vector. Serum and stool samples were assayed by ELISA for VP6 antigen specific serum IgG and intestinal IgA respectively every two weeks for twelve weeks.

Figure 10:
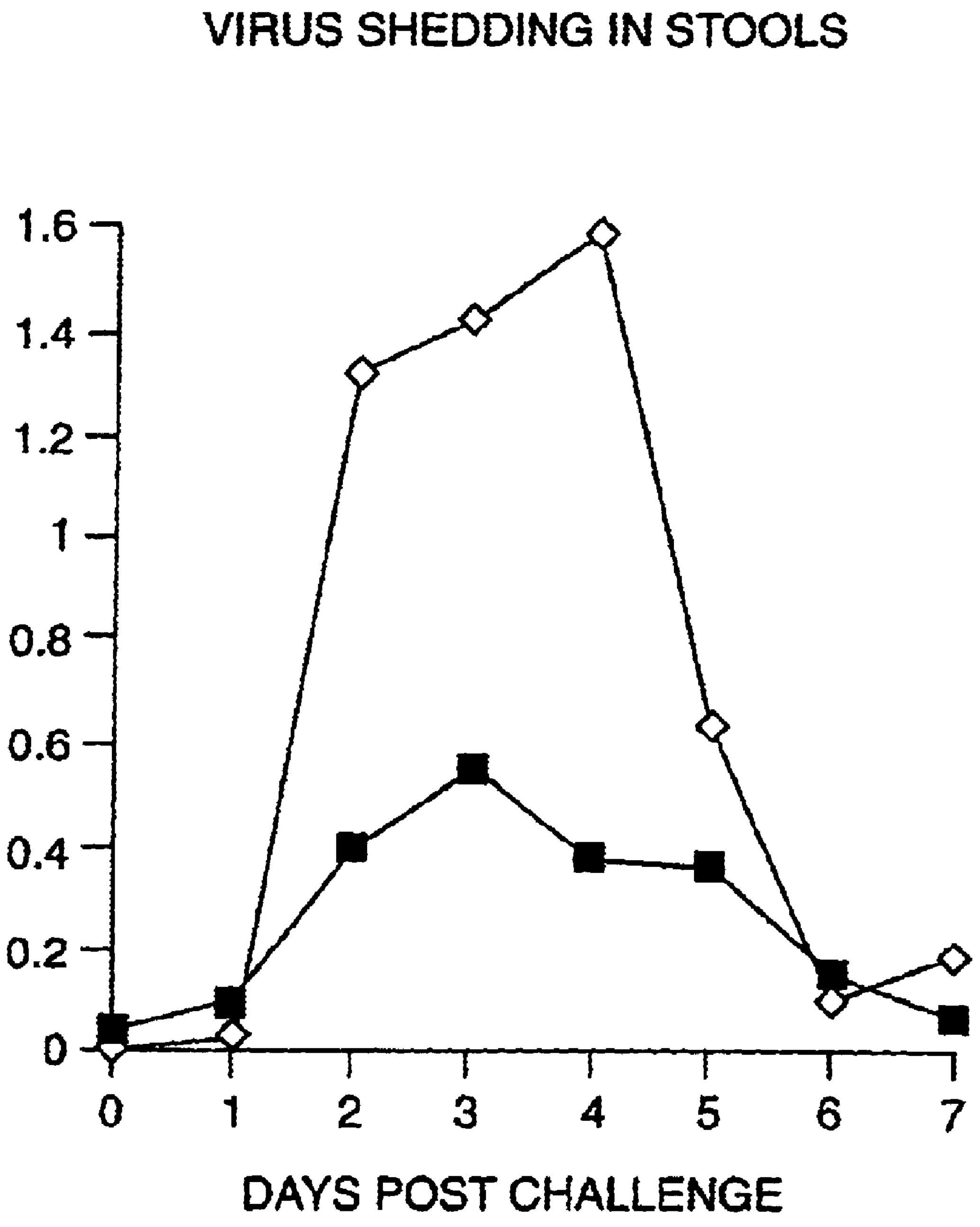
FIG. 10 shows animal protection data showing the protection of mice from Rotavirus challenge after oral immunisation with PLG encapsulated pDNA encoding the Rotavirus PV6 protein.

All mice were challenged with 100 $ID_{50}$ of a homotypic murine rotavirus (EDIM) at twelve weeks post immunisation to assess levels of vaccine induced protection. The experimental results, expressed as ELISA values for the detection of rotavirus antigen shedding in stools, are shown in FIG. 10. In this example a significant reduction in the viral load was observed on days 2, 3, and 4, compared with the levels seen in groups of control mice. The protection after a single dose of oral plasmid DNA vaccine is very significant suggesting that, once optimised, this formulation and route of delivery could be-an effective alternative to directly injected or trans-dermally delivered plasmid vaccines.

Example 14

We carried out a series of further encapsulations to investigate the effects of varying the temperature at which the organic polymer solvent is dispersed and the effects of altering temperature and alcohol concentration during the steps of forming the double emulsion of aqueous DNA in organic polymer plus solvent in aqueous surfactant.

First, steps 1–3 were performed as in examples 1, 8 and 9 and then step 4, in which the double emulsion is combined with water so as to disperse the organic polymer solvent, was carried out using water at a temperature of about 18° C. Instead of forming microparticles, this step resulted in formation of an agglomerated mass of polymer.

Next we repeated the DNA encapsulation using an elevated temperature, namely 30–35° C., for the step of dispersing the organic polymer solvent, and found that microparticles were formed with good efficiency and in the desired size range. These results followed those of Example 9 in which reduced temperature of emulsion formation followed by dispersal of solvent at ambient temperature also showed improved DNA uptake compared to when emulsion forming and solvent dispersing steps are carried out at the same temperature.

Subsequently, we carried out a series of encapsulations using this elevated dispersal temperature and varying the ethanol content and the temperature of the emulsion-forming steps.

These encapsulations were performed by mixing 0.45 ml of 5 mg/ml pDNA in 100 mM NaCl, 10 mM tris, 1 mM EDTA, pH8.0, with 0.15 ml of water/ethanol to give a final ethanol concentration of 0, 10 or 25%. These were then cooled to the appropriate temperature (see below) and emulsified at 2,000 rpm with a Silverson mixer for 2½ minutes with 3 ml of 133 mg/ml PLG in dichloromethane, again at the appropriate temperature. The emulsion was then emulsified for 2½ minutes at 2,000 rpm with 72 ml of 8% PVA, again at the appropriate temperature. The resultant double emulsion was then added to 100 ml of water at 35° C. and then centrifuged to recover microparticles according to the details in examples 1, 8 and 9.

The results were as follows:

| Ethanol/Emulsion-Forming Temperature | 21° C. | 12° C. | 6° C. | 0° C. |
|---|---|---|---|---|
| 0% | 36% | 50% | 34% | 6% |
| 10% | 31% | 8.8% | 7% | 6.2% |
| 25% | 8.5% | — | 5% | 5% |

These results show that when elevated dispersal temperature is used then a lower ethanol concentration, or no ethanol at all, can be used to obtain efficient encapsulation of DNA.

The compositions and methods of the invention have application in slow release systems for delivery of DNA vaccines; prolonged expression of immunogen potentially results in efficient single dose priming and boosting, with consequent efficient induction of long term memory responses. Another application is in a vehicle for the oral delivery of vaccines; simple and acceptable means for vaccine administration are likely to improve vaccine uptake rates; in addition, freeze-dried encapsulated plasmid DNA is likely to be very stable and insensitive to environmental conditions. A further application is in a slow release system for gene therapy; prolonged release of DNA and subsequent expression potentially reduces the need for repeated treatment.

TABLE 1

ACCESSION NUMBERS OF GENE SEQUENCES IDENTIFIED AS PUTATIVE OR PROTECTIVE ANTIGENS AGAINST SPECIFIC PATHOGENS

| Organism | Protein/Glycoprotein | Accession Number | Database |
|---|---|---|---|
| Bordetella Pertussis | FHA; PT | P12255; M13223 | Swiss Prot; Genbank |
| Bordetella Bronchiseptica | 68kd-Pertactin | X54815 | Genbank |
| Clostridium Tetani | Tetanus Toxin | P04958 | Genbank |
| CMV | gp48 | A32390 | Swiss Prot |
| Dengue Virus | NS1; Capsid | S37468; Z794047 | Swiss Prot |
| EBV | gp350 | A43042; S33008; A03762 | Swiss Prot |
| Flavivirus | NS3 | S79821; S79825; S79826; S79830 | |
| Hepatitis B Virus | SA | V00867; X02763 | Genbank |
| Herpes Simplex Virus | I | P06487 | Genbank |
| Influenza Virus | NP | H36754 | Swiss Prot |
| JEV | E; M; gp340 | M18370 | Swiss Prot |
| Measles Virus | F; H | D00090; N00090; Z80790 | Genbank |
| Mumps Virus | HN | X93178 | Genbank |
| Mycobacteria Tuberculosis | 35kd protein | M69187 | Genbank |
| Rotavirus | VP1 | P35942 | Swiss Prot |
| Rubella Virus | E1; E2 | A27505; D00156 | Swiss Prot, Genbank |
| TBE | C; M; E | X07755; M97369 | Genbank |
| Vibrio Cholerae | MSHA | X77217 | Genbank |

What is claimed is:

1. A composition comprising a polymer microparticle and an aqueous solution of DNA, wherein the DNA comprises a coding sequence, wherein the microparticle is 10 μm or less in diameter, and wherein the aqueous solution of DNA has an alcohol content of 1 to 40% and is encapsulated inside the microparticle.

2. The composition according to claim 1, wherein the microparticle comprises a biodegradable polymer.

3. The composition according to claim 2, wherein the polymer is selected from the group consisting of a lactide-containing polymer, a glycolide-containing polymer and a polymer comprising lactide and glycolide.

4. The composition according to claim 2, wherein the polymer is soluble in an organic solvent.

5. The composition according to claim 1, wherein the microparticle consists of a biodegradable polymer.

6. The composition according to claim 5, wherein the polymer is selected from the group consisting of a lactide-containing polymer, a glycolide-containing polymer and a polymer comprising lactide and glycolide.

7. The composition according to claim 1, wherein the microparticle is in the size range 0.1 μm to 10 μm.

8. The composition according to claim 1, wherein the DNA is circular DNA or plasmid DNA.

9. The composition according to claim 1, wherein the DNA further comprises a promoter sequence operably linked to the coding sequence.

10. The composition according to claim 9, wherein the coding sequence encodes an immunogen.

11. The composition according to claim 10, wherein the coding sequence encodes an immunogenic component of a pathogenic organism selected from the group consisting of pathogenic bacteria and pathogenic viruses.

12. A pharmaceutical composition comprising a plurality of polymer microparticles and a pharmaceutically acceptable carrier, wherein the microparticles contain an aqueous solution of DNA the aqueous solution of DNA has an alcohol content of 1 to 40%, and the DNA comprises a coding sequence encoding a polypeptide selected from the group consisting of:

(a) the antigens FHA, PT, 68 kd-Pertacin, tetanus toxin, gp-48, NS1, Capsid, gp350, NS3, SA, I, NP E, M, gp340, F, H, HN, 35 kd protein, VP1, E1, E2, C, M, E and MSHA; and (b) immunogenic fragments, of the polypeptides of (a).

13. The composition according to claim 12 wherein the microparticles are in the size range 0.1 μm to 10 μm.

14. The composition according to claim 13, wherein the DNA comprises double stranded plasmid DNA.

15. The composition according to claim 14, wherein the DNA further comprises a promoter sequence operably linked to the coding sequence.

16. The composition according to claim 12, wherein the polymer is a lactide containing polymer.

17. The composition according to claim 12, wherein the polymer is a glycolide-containing polymer.

18. The composition according to claim 12, wherein the polymer comprises poly(DL-lactide-co-glycolide).

19. The composition according to claim 12 wherein at least 50% of the microparticles are in the size range 0.1 μm to 10 μm.

20. The composition according to claim 12, further comprising a taste-enhancing agent.

21. The composition of claim 1, wherein the alcohol is a straight chain or branched $C_2$–$C_{10}$ alcohol.

22. The composition of claim 1, wherein the alcohol is ethanol.

23. The composition of claim 1, wherein the alcohol is methanol or propanol.

24. The pharmaceutical composition of claim 12, wherein the alcohol is a straight chain or branched $C_2$–$C_{10}$ alcohol.

25. The pharmaceutical composition of claim 12, wherein the alcohol is ethanol.

26. The pharmaceutical composition of claim 12, wherein the alcohol is methanol or propanol.

* * * * *